United States Patent
Zhang et al.

(10) Patent No.: US 11,890,618 B2
(45) Date of Patent: Feb. 6, 2024

(54) MAGNETIC DIGITAL MICROFLUIDIC APPARATUS AND METHOD OF MAGNETIC DIGITAL MICROFLUIDIC MANIPULATION

(71) Applicant: Nanyang Technological University, Singapore (SG)

(72) Inventors: Yi Zhang, Singapore (SG); Pojchanun Kanitthamniyom, Singapore (SG)

(73) Assignee: Nanyang Technological University, Singapore (SG)

( * ) Notice: Subject to any disclaimer, the term of this patent is extended or adjusted under 35 U.S.C. 154(b) by 637 days.

(21) Appl. No.: 17/049,103

(22) PCT Filed: Apr. 23, 2019

(86) PCT No.: PCT/SG2019/050225
§ 371 (c)(1),
(2) Date: Oct. 20, 2020

(87) PCT Pub. No.: WO2019/209178
PCT Pub. Date: Oct. 31, 2019

(65) Prior Publication Data
US 2021/0237081 A1    Aug. 5, 2021

(30) Foreign Application Priority Data
Apr. 25, 2018   (SG) ........................ 10201803454W

(51) Int. Cl.
*B01L 3/00* (2006.01)
*G01N 33/543* (2006.01)
(Continued)

(52) U.S. Cl.
CPC .... *B01L 3/502792* (2013.01); *B01F 33/3021* (2022.01); *B01F 33/30351* (2022.01);
(Continued)

(58) Field of Classification Search
CPC ......... B01L 2300/161; B01L 2400/043; B01L 3/50273; B01L 3/502792;
(Continued)

(56) References Cited

U.S. PATENT DOCUMENTS

| 2013/0303394 A1* | 11/2013 | Wang .................... B01L 3/5085 435/6.12 |
| 2015/0038364 A1* | 2/2015 | Zheng .................... C40B 40/06 506/13 |
| 2018/0100853 A1 | 4/2018 | Zhang et al. |

FOREIGN PATENT DOCUMENTS

| CN | 107522827 A | 12/2017 |
| WO | 2019209178 A1 | 10/2019 |

OTHER PUBLICATIONS

Seo et al. Path-programmable water droplet manipulations on an adhesion controlled superhydrophobic surface. Sci Rep 5, 12326 ( (Year: 2015).*

(Continued)

*Primary Examiner* — Christine T Mui
*Assistant Examiner* — Jonathan Bortoli
(74) *Attorney, Agent, or Firm* — Conley Rose, P.C.

(57) ABSTRACT

A magnetic digital microfluidic apparatus for manipulating a liquid droplet containing magnetic particles using a magnetic force, the apparatus comprising: a hydrophobic surface on which the liquid droplet containing magnetic particles can be moved using the magnetic force; and at least one surface energy trap provided to retain at least a portion of the liquid droplet thereon, the at least one surface energy trap comprising a layer of polydopamine. A method of magnetic digital microfluidic manipulation, the method comprising the steps of:
a) contacting a liquid droplet on a hydrophobic surface with a polydopamine surface energy trap, the liquid droplet containing magnetic particles;
(Continued)

b) retaining at least a portion of the liquid droplet on the surface energy trap; and c) moving at least the magnetic particles with a magnetic force.

18 Claims, 15 Drawing Sheets

(51) Int. Cl.
| | |
|---|---|
| B01F 33/451 | (2022.01) |
| B01F 33/302 | (2022.01) |
| B01F 33/30 | (2022.01) |
| B01F 101/23 | (2022.01) |

(52) U.S. Cl.
CPC ........ *B01F 33/451* (2022.01); *B01L 3/50273* (2013.01); *G01N 33/54326* (2013.01); *B01F 2101/23* (2022.01); *B01L 2300/161* (2013.01); *B01L 2400/043* (2013.01); *G01N 2333/02* (2013.01)

(58) Field of Classification Search
CPC ......... B01L 2300/0816; B01L 2300/12; B01L 2400/088; G01N 2333/02; G01N 33/54326; B01F 2101/23; B01F 33/3021; B01F 33/30351; B01F 33/451; H04J 11/0069; H04L 41/0806; H04L 5/0048; H04W 16/14; H04W 48/10; H04W 56/00; H04W 56/001; H04W 72/0446; H04W 72/12; H04W 74/08; H04W 74/0808
See application file for complete search history.

(56) References Cited

OTHER PUBLICATIONS

Foreign Communication from a Related Counterpart Application, International Search Report and Written Opinion dated Jul. 5, 2019, International Application No. PCT/SG2019/050225 filed on Apr. 23, 2019.
Kanitthamniyom P & Zhang Y., Application of polydopamine in biomedical microfluidic devices. Microfluidics and Nanofluidics, Feb. 13, 2018, vol. 22, No. 3, Article No. 24 [Retrieved on Jun. 28, 2019] <DOI: 10.1007/S10404-018-2044-6> whole document, particularly fig. 3-5 and section 2.2.
Feng H. et al., Ultralow background substrate for protein microarray technology. Analyst., Aug. 21, 2015, vol. 140, No. 16, pp. 5627-5633 [Retrieved on Jun. 28, 2019] <DOI: 10.1039/C5AN00852B> fig. 1, 4; section of "solution dispensing on the patterned FEP".
Kanitthamniyom P & Zhang Y., Magnetic digital microfluidics on a bioinspired surface for point-of-care diagnosis of infe3ctious disease, Electrophoresis, Feb. 16, 2019, vol. 40, No. 8, pp. 1178-1185 [Retrieved on Jun. 28, 2019] <DOI: 10.1002/ELPS.201900074>.
Pipper, J., et al, "Catching bird flu in a droplet", Nature Medicine, Technical Reports, vol. 13, No. 10, Oct. 2007, pp. 1259-1263, Published Sep. 23, 2007, <DOI: 10.1038/nm1634>.
Miller, E., et al. "A Digital Microfluidic Approach to Homogeneous Enzyme Assays", Analytical Chemistry, vol. 80, No. 5, Mar. 1, 2008, pp. 1614-1619, <DOI: 10.1021/ac702269d>.
Shamsi, M., et al., "A digital microfluidic electrochemical immunoassay", The Royal Society of Chemistry, Lab Chip, 2014, pp. 547-554, <DOI: 10.1039/c3lc51063h>.
Zhang, Y., et al. "A surface topography assisted droplet manipulation platform for biomarker detection and pathogen dentification", The Royal Society of Chemistry, Lab Chip, 2011, pp. 398-406, <DOI: 10.1039/c01c00296h>.

Zhao, Y., et al., "Magnetic Liquid Marbles: Manipulation of Liquid Droplets Using Highly Hydrophobic FE3O4 Nanoparticles", Advanced Materials, Materials Views, 2010, pp. 7070-7710, <DOI: 10.1002/adma.200902512>.
Xu, F., et al., "Three-Dimensional Magnetic Assembly of Microscale Hydrogels", Advanced Materials, Materials Views, 2011, pp. 4254-4260, <DOI: 10.1002/adma.201101962>.
Kim, B. H., et al., "Mussel-Inspired Block Copolymer Lithography for Low Surface Energy Materials of Teflon, Graphene, and Gold", Advanced Materials, Materials Views, 2011, pp. 5618-5622, <DOI: 10.1002/adma.201103650>.
Tasoglu, S., "Paramagnetic Levitational Assembly of Hydrogels", Advanced Materials, Materials Views, 2013, pp. 1137-1143, <DOI: 10.1002/adma.201200285>.
Yazdani, Y., et al., "Development of a Sensitive Enzyme-Linked Immunosorbent Assay for Detection of Hepatits B Surface Antigen Using Novel Monoclonal Antibodies". Avicenna Journal of Medical Biotechnology, vol. 2, No. 4, Oct.-Dec. 2010, pp. 207-214.
Abdelgawad, M., et al., "All-terrain droplet actuation", The Royal Society of Chemistry, Lab Chip, 2008, pp. 672-677, <DOI: 10.1039/b801516c>.
Pipper, J., et al., "Clockwork PCR Including Sample Preparation", Angewandte Chemie Int. Ed. 2008, pp. 3900-3904, <DOI: 10.1002/anie.200705016>.
Choi, K., et al., "Digital Microfluidics", Annual Review of Analytical Chemistry, 2012, pp. 413-440, <DOI: 10.1146/annurev-anchem-062011-143028>.
Yeo, L., et al., "Surface Acoustic Wave Microfluidics", Annual Review of Fluid Mechanics, 2014, pp. 379-406, <DOI: 10.1146/annurev-fluid-010313-141418>.
Pollack, M., et al., "Applications of electrowetting-based digital microfluidics in clinical diagnostics", Expert Review of Molecular Diagnostics, 2011, 11:4, 393-407, <DOI: 10.1586/erm.11.22>.
Ye, Q., et al., "Bioinspired catecholic chemistry for surface modification", The Royal Society of Chemistry, 2011, pp. 4244-4258, <DOI: 10.1039/c1cs15026j>.
Shen, B., et al., "Convenient surface functionalization of whole-Teflon chips with polydopamine coating", Biomicrofluidics, American Institute of Physics, 2015, <DOI: 10.1063/1.4927675>.
Ng, A., et al., "Digital microfluidic immunocytochemistry in single cells", Nature Communications, Jun. 24, 2015, <DOI: 10.1038/ncomms8513>.
R. B. Fair, "Digital microfluidics: is a true lab-on-a-chip possible", Micro Nanofluid, Mar. 8, 2007, <DOI: 10.1007/s10404-007-0161-8>.
Long, Z., et al., "Fundamentals of magnet-actuated droplet manipulation on an open hydrophobic surface", Lab on a Chip, The Royal Society of Chemistry, Mar. 9, 2009, pp. 1567-1575, <DOI: DOI: 10.1039/b819818g>.
Tasoglu, S., et al., "Guided and magnetic self-assembly of tunable magnetoceptive gels", Nature Communications, Sep. 1, 2014, <DOI: 10.1038/ncomms5702>.
Chan, H., et al., "Hepatitis B surface antigen quantification: Why and how to use it in 2011—A core group report", Journal of Hepatology, 2011, vol. 55, pp. 1121-1131.
Se-Ho Kim, "ELISA for Quantitative Determination of Hepatitis B Virus Surface Antigen", Immune Network, 2017, <DOI: 10.4110/in.2017.17.6.451>.
Sonneveld, M. J., et al., "Hepatitis B surface antigen monitoring and management of chronic hepatitis B", Journal of Viral Hepatitis, Apr. 2011, 18, pp. 449-457, <doi:10.1111/j.1365-2893.2011.01465.x>.
Zhang, Y., et al., "Magnetic digital microfluidics—a review", Lab on a Chip, The Royal Society of Chemistry, vol. 17, No. 6, Mar. 21, 2017, pp. 965-1168, <DOI: 10.1039/c7lc00025a>.
Lee, B., et al., "Mussel-Inspired Adhesives and Coatings", NIH Public Access, Annu Rev Mater Res. Aug. 1, 2011; 41: pp. 99-132, <doi:10.1146/annurev-matsci-062910-100429>.
Zhang, Y., et al., "Serial Dilution via Surface Energy Trap-Assisted Magnetic Droplet Manipulation", NIH Public Access, Lab Chip. Dec. 21, 2013; 13(24): pp. 4827-4831. <doi:10.1039/c3lc50915j>.
Sundaram, H., et al., "One-Step Dip Coating of Zwitterionic Sulfobetaine Polymers on Hydrophobic and Hydrophilic Surfaces", Applied

(56) References Cited

OTHER PUBLICATIONS

Materials and Interfaces, American Chemical Society, Apr. 15, 2014, <doi: 10.1021/am500362k>.
Kang, S., et al., "One-Step Multipurpose Surface Functionalization by Adhesive Catecholamine", NIH Public Access, Adv Funct Mater. Jul. 24, 2012; 22(14): pp. 2949-2955, <doi:10.1002/adfm.201200177>.
Guttenberg, Z., et al., "Planar chip device for PCR and hybridization with surface acoustic wave pump", Lab on a Chip, The Royal Society of Chemistry, 2005, 5, pp. 308-317, <DOI: 10.1039/b412712a>.
Kanitthamniyom, P., et al., "Magnetic digital microfluidics on a bioinspired surface for point-of-care diagnostics of infectious disease", Electrophoresis, 2019, 40, pp. 1178-1185, <DOI 10.1002/elps.201900074>.
Yang, H., et al., "Polydopamine gradients by oxygen diffusion controlled autoxidation", ChemComm, Communication, The Royal Society of Chemistry, 2013, pp. 10522-10524, <DOI: 10.1039/c3cc46127k>.
You, I., et al., "Polydopamine Microfluidic System toward a Two-Dimensional, Gravity-Driven Mixing Device", Angewandte Communications, 2012, 51, pp. 6126-6130, <DOI: 10.1002/anie.201200329>.
Salazar, P., et al., "Polydopamine-modified surfaces in biosensor applications", ResearchGate, 2016, pp. 385-396.
Wang, Z., et al., "Recent advances in particle and droplet manipulation for lab on-a-chip devices based on surface acoustic waves", Lab on a Chip, The Royal Society of Chemistry, 2011, pp. 1280-1285, <DOI: 10.1039/c0lc00527d>.
Shikida, M., et al., "Development of an enzymatic reaction device using magnetic bead-cluster handling", Journal of Micromechanics and Microengineering, 2006, pp. 1875-1883, <doi:10.1088/0960-1317/16/9/017>.
Shikida, M., et al., "A palmtop-sized rotary-drive-type biochemical analysis system by magnetic bead handling", Journal of Micromechanics and Microengineering, 2008, <doi:10.1088/0960-1317/18/3/035034>.
Ding, X., et al., "Surface acoustic wave microfluidics", Lab Chip, The Royal Society of Chemistry, 2013, 13, 3626-3649, <DOI: 10.1039/c3lc50361e>.
Zhang, E., et al., "Surface and Tribological Behaviors of the Bioinspired Polydopamine Thin Films under Dry and Wet Conditions", Biomacromolecules, American Chemical Society, 2013, 14, pp. 394-405, <doi: 10.1021/bm3015768>.
Jiang, J., et al., "Surface Characteristics of a Self-Polymerized Dopamine Coating Deposited on Hydrophobic Polymer Films", Langmuir, American Chemical Society, 2011, 27, pp. 14180-14187, <doi: 10.1021/la202877k>.
Ng, A., et al., "Digital Microfluidic Magnetic Separation for Particle-Based Immunoassays", Analytical Chemistry, American Chemical Society, 2012, 84, pp. 8805-8812, <doi: 10.1021/ac3020627>.
Zhang, Y., et al., "Full-Range Magnetic Manipulation of Droplets via Surface Energy Traps Enables Complex Bioassays", Advanced Materials, 2013, 25, pp. 2903-2908, <DOI: 10.1002/adma.201300383>.
Vincent Ball, "Physicochemical perspective on 'polydopamine' and 'poly(catecholamine)' films for their applications in biomaterial coatings (Review)", Biointerphases, 9(3), Sep. 2014, <doi: 10.1116/1.4875115>.
Shen, B., et al., "Convenient surface functionalization of whole-Teflon chips with polydopamine coating", Biomicrofluidics, 9, 2015, <doi: 10.1063/1.4927675>.
Lee, H., et al., "Mussel-Inspired Surface Chemistry for Multifunctional Coatings", Science, vol. 318, pp. 426-430, 2007, <DOI: 10.1126/science.1147241>.
Cheng, G., et al., "Construction of a high-performance magnetic enzyme nanosystem for rapid tryptic digestion", Scientific Reports, 2014, <DOI: 10.1038/srep06947>.
Salazar, P., et al., "Polydopamine-modified surfaces in biosensor applications", Polymer science: research advances, practical applications and educational aspects.
Chiou, C., et al., "Topography-assistedelectromagneticplatformforblood-to-PCR in a droplet", Biosensors andBioelectronics, 50, 2013, pp. 91-99, <doi: 10.1016/j.bios.2013.06.011>.
Lehmann, U., et al., "Two-dimensional magnetic manipulation of microdroplets on a chip as a platform for bioanalytical applications", ScienceDirect, 2006, pp. 457-463, <DOI: 10.1016/j.snb.2005.12.053>.
Zhao, Y., et al., "Magnetic liquid marbles, their manipulation and application in optical probing", Microfluid Nanofluid, 2012, 13, pp. 555-564, <DOI 10.1007/s10404-012-0976-9>.
Foreign Communication from a Related Counterpart Application, Chinese Office Action dated Nov. 2, 2021, Chinese Application No. 201980028136.4 filed on Apr. 23, 2019.
China's Strategic Emerging Industry-New Materials "High-performance separation membrane material", Zhikang Xu, et al. pp. 96-97, China Railway Press, Dec. 2017.

\* cited by examiner

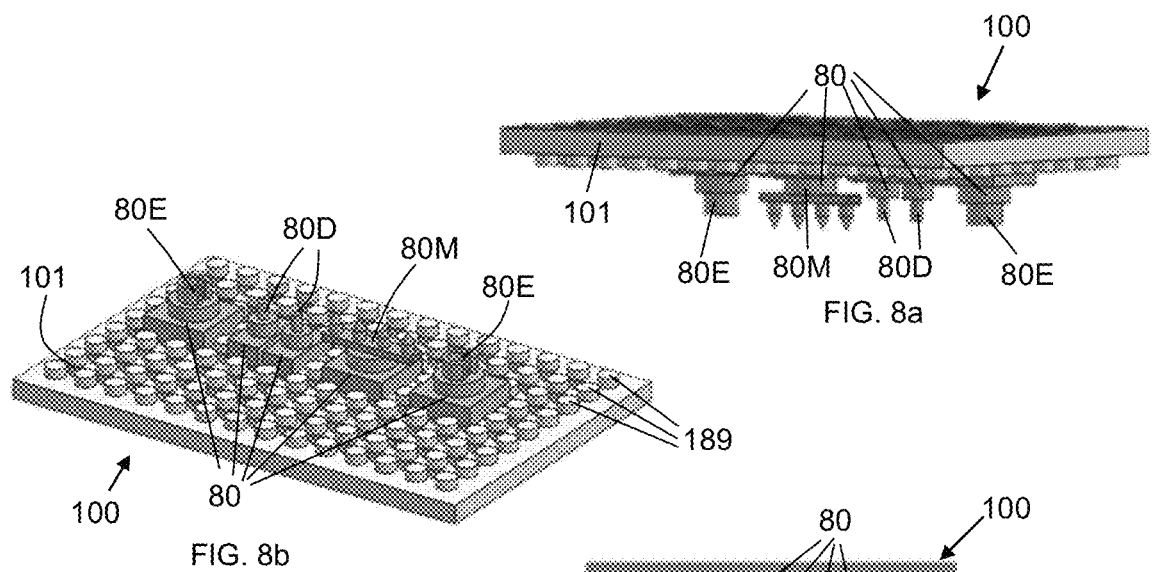
FIG. 8a
FIG. 8b
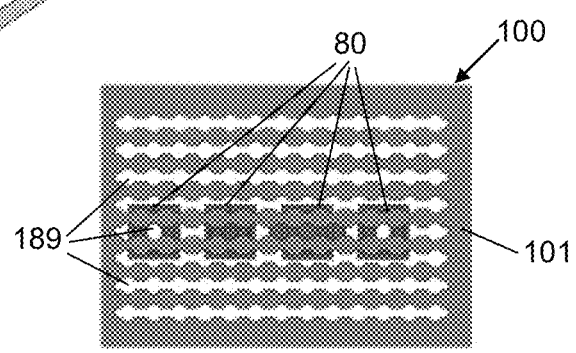
FIG. 8c
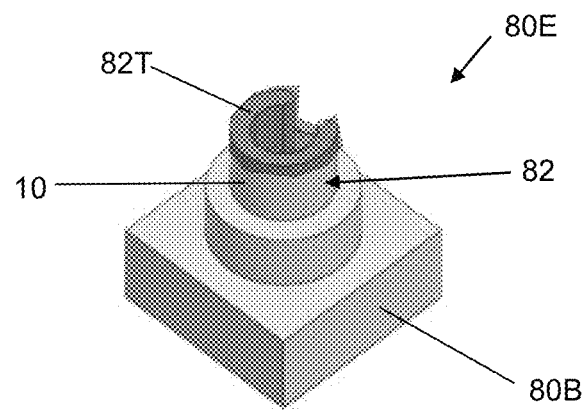
FIG. 9a

MAGNETIC DIGITAL MICROFLUIDIC APPARATUS AND METHOD OF MAGNETIC DIGITAL MICROFLUIDIC MANIPULATION

CROSS-REFERENCE TO RELATED APPLICATIONS

The present application is a filing under 35 U.S.C. 371 as the National Stage of International Application No. PCT/SG2019/050225, filed Apr. 23, 2019, entitled "MAGNETIC DIGITAL MICROFLUIDIC APPARATUS AND METHOD OF MAGNETIC DIGITAL MICROFLUIDIC MANIPULATION," which claims priority to Singapore Application No. 10201803454W filed with the Intellectual Property Office of Singapore on Apr. 25, 2018, both of which are incorporated herein by reference in their entirety for all purposes.

FIELD

This invention relates to a magnetic digital microfluidic apparatus and method of magnetic digital microfluidic manipulation.

BACKGROUND

In digital microfluidics, discrete volumes of fluid are manipulated on an open surface where the fluid forms droplets on a hydrophobic surface, such as a surface coated with polytetrafluoroethylene (PTFE, also known as Teflon™). Depending on the droplet manipulation mechanism, some examples of digital microfluidics include electrowetting-on-dielectric (EWOD) and magnetic digital microfluidics. Among these digital microfluidic platforms, magnetic digital microfluidics is particularly well-suited for point-of-care diagnostics due to its simple droplet manipulation and the multi-functionality of the magnetic particles that are added into droplets as the droplet actuator in a magnetic digital microfluidic platform. When an external magnetic force is applied, for example via a magnetic field provided by a permanent magnet or an electric magnet, the magnetic particles translocate under the influence of the magnetic field gradient and drag the droplet along with them. Although the motion control is not as accurate as EWOD, this magnetic actuation mechanism is easier to implement. A small permanent magnet is often sufficient to perform all the fluidic operations required for a diagnostic assay. As a result, no complex control system is required for fluidic operation on magnetic digital microfluidic platform. Therefore, magnetic digital microfluidics is better suited for point-of-care diagnostics in low-resource environments. The droplets on a magnetic digital microfluidic platform are self-contained and function as virtual reaction chambers in which diagnostic assays are carried out. One unique advantage of magnetic digital microfluidics is the multi-functionality of the magnetic particles. In addition to functioning as the droplet actuator, the magnetic particles also serve as the functional substrate for solid-phase biochemical reactions. For example, magnetic particles with silica coating reversely bind with DNA molecules under different buffer conditions and are commonly used for DNA extraction in magnetic digital microfluidic. Magnetic particles labeled with antibodies are used to detect the target of interest through enzyme-linked immune sorbent assay (ELISA) in droplets.

In its simplest form, the substrate of the magnetic digital microfluidic platform is typically a plain surface coated with Teflon™ which renders the surface hydrophobic to facilitate droplet movement. In order to perform complex bioassays that require a wide range of droplet-based fluidic operations, many additional features, either in the form of physical structures or chemical modifications, must be introduced to the Teflon™-coated substrate. These features enable intricate droplet manipulations on the magnetic digital microfluidic platform for more complex bioanalytical assays to be performed.

In a droplet-based solid phase heterogeneous assay, magnetic particles must be extracted from one droplet and merged with another droplet for washing and other processes that require liquid exchange. On the conventional magnetic digital microfluidic platform, magnetic particle extraction is realized by increasing its moving speed. However, if the moving speed is too high, the magnet would disengage from the magnetic particles and droplets. To solve this problem, several magnetic digital microfluidic platforms introduced microstructures to the plain surface, such as a slit or a narrow channel. These structures would constrain the droplet movement while allowing the magnetic particles to pass through, thereby facilitating extraction of the magnetic particles from the droplet. However, the fabrication and surface modification of these physical structures on a magnetic digital microfluidic platform present certain challenges.

As an alternative, chemical modification methods are used to create hydrophilic regions on the Teflon™-coated hydrophobic surface. These hydrophilic regions, known as surface energy traps, would immobilize the droplet with their high surface tension to facilitate extraction of magnetic particles from the droplet. If the size of a surface energy trap is relatively small compared to the droplet, the surface energy trap would withhold a small portion of the liquid as the droplet moves over with magnetic particles. This mechanism is thus also used to dispense liquid for aliquoting and serial dilution. As a result, the magnetic digital microfluidic platform with chemically modified surface energy traps is able to perform a full range of fluidic operations and conduct complex heterogeneous and multiplexed bioassays in droplets.

However, chemical modification to create hydrophilic regions on a hydrophobic Teflon™-coated surface relies on oxygen plasma treatment and has several limitations that hinder its application in patterning surface energy traps on the Teflon™-coated surface. First, because the Teflon™-coated surface is non-wettable by photoresist, the surface energy traps must be patterned through a lithographically defined SU-8 shadow mask fabricated using a liftoff process. However, the SU-8 shadow mask is brittle and difficult to handle, and also takes great effort to be fabricated while being able to be used only for a limited number of times before it is broken. Second, while the oxygen plasma treatment etches away the Teflon™ in regions not protected by the shadow mask and grafts on a hydroxyl group to render the underlying substrate (e.g. glass or silicon) hydrophilic, the hydrophilic effect obtained by oxygen plasma treatment is only temporary, lasting for a couple of days at most. Subsequently, the substrate would gradually lose its hydrophilicity and the surface energy traps would no longer be able to provide high enough surface tension to anchor the droplet for magnetic particle extraction and liquid dispensing.

SUMMARY

The present application discloses an easy method of patterning hydrophilic regions on a Teflon™-coated surface for magnetic digital microfluidics using highly adhesive bioinspired material known as polydopamine. In laboratory settings, polydopamine is synthesized by polymerizing catechol, such as 3,4-dihydroxy-L-phenylalanine (DOPA) or dopamine HCL, in an alkaline environment. Polydopamine adheres to surfaces of almost any material, including Teflon™ which is non-wettable by aqueous solution. To apply a polydopamine coating, an alkaline solution of dopamine monomer is placed on the Teflon™-coated substrate where the dopamine monomers would spontaneously polymerize and form a polydopamine thin film adherent strongly to the surface. This polydopamine coating is hydrophilic with many hydroxyl, carboxyl and other functional groups. Consequently, biomolecules such as proteins and peptides can be directly grafted to the polydopamine modified surface with a great ease. In addition, the polydopamine coating has adequate reducing capability to reduce noble metal ions to form a metal coating. The present application also discloses a magnetic digital microfluidic apparatus that allows manipulation by magnetic force of droplets containing magnetic particles on a bioinspired surface modified with polydopamine for the diagnoses of infectious diseases. A method is disclosed for forming patterns on the Teflon™-coated surface with polydopamine, which creates hydrophilic surface energy traps to facilitate droplet manipulation on the hydrophobic surface. The interplay between the surface tension from the surface energy traps and the magnetic force empowers a wide range of droplet operations including particle extraction, liquid dispensing, liquid shaping and cross-platform liquid transfer on the polydopamine-modified magnetic digital microfluidic platform. On this platform, a proof-of-concept of the hepatitis B diagnostics by detecting the hepatitis B surface antigen (HBsAg) using particle-based ELISA in droplets was demonstrated.

According to a first aspect, there is provided a magnetic digital microfluidic apparatus for manipulating a liquid droplet containing magnetic particles using a magnetic force, the apparatus comprising: a hydrophobic surface on which the liquid droplet containing magnetic particles can be moved using the magnetic force; and at least one surface energy trap provided to retain at least a portion of the liquid droplet thereon, the at least one surface energy trap comprising a layer of polydopamine.

In use, the at least one surface energy trap may retain all of the liquid droplet thereon while allowing the magnetic particles to be moved out of the liquid droplet by the magnetic force.

In use, the at least one surface energy trap may retain only a part of the liquid droplet thereon while allowing a remainder of the liquid droplet containing the magnetic particles to be moved away from the droplet manipulator by the magnetic force.

The at least one surface energy trap may be formed on the hydrophobic surface on which the liquid droplet containing magnetic particles can be moved.

The apparatus may further comprise at least one droplet manipulator provided on a platform, wherein the at least one hydrophilic surface energy trap is formed on the at least one droplet manipulator.

The at least one droplet manipulator may be releasably attachable to the platform.

The surface energy trap may be formed at a tip of a projection of the droplet manipulator.

The projection may have a C-shaped cross-section. Alternatively, a hole may be provided at the tip and the surface energy trap may be formed in the hole.

The apparatus may further comprise at least one mixing droplet manipulator provided on a platform to facilitate mixing of liquid in the liquid droplet.

The at least one mixing droplet manipulator may be releasably attachable to the platform.

The mixer droplet manipulator may comprise a plurality of hydrophobic projections provided to pass through the liquid droplet The apparatus may further comprise at least one transferring droplet manipulator provided on a platform to facilitate transfer of at least one liquid droplet from one hydrophobic surface to another hydrophobic surface.

The at least one transferring droplet manipulator may be releasably attachable to the platform.

The transferring droplet manipulator may comprise at least one surface energy trap to remove and retain at least one liquid droplet from another surface.

The at least one droplet manipulator may be releasably attachable to the platform at any one of a plurality of selectable locations on the platform.

A shape of the portion of the liquid droplet retained by the at least one surface energy trap may conform with a shape of the at least one surface energy trap.

According at a second aspect, there is provided a method of magnetic digital microfluidic manipulation, the method comprising the steps of:
 a) contacting a liquid droplet on a hydrophobic surface with a polydopamine surface energy trap, the liquid droplet containing magnetic particles;
 b) retaining at least a portion of the liquid droplet on the surface energy trap; and
 c) moving at least the magnetic particles with a magnetic force.

Step (b) may comprise retaining all of the liquid droplet on the surface energy trap and step (c) may comprise moving the magnetic particles out of the liquid droplet retained on the surface energy trap.

Alternatively, step (b) may comprise retaining only a part of the liquid droplet on the surface energy trap and step (c) may comprise moving a remainder of the liquid droplet and the magnetic particles away from the part of the liquid droplet retained on the surface energy trap.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

FIG. 7b is a schematic view of an antibody-conjugated magnetic bead used in the liquid droplets shown in FIG. 7a.

FIG. 8a is a side perspective view of an exemplary magnetic digital microfluidic apparatus comprising droplet manipulators attached to a platform.

FIG. 8b is a bottom perspective view of the apparatus of FIG. 8a.

FIG. 8c is a top view of the apparatus of FIG. 8a.

FIG. 9a is a bottom perspective view of a droplet manipulator configured to facilitate magnetic particle extraction from a liquid droplet.

FIG. 9b is a top perspective view of the droplet manipulator of FIG. 9a.

FIG. 10b is a top perspective view of the droplet manipulator of FIG. 10a.

DETAILED DESCRIPTION

Figure 1A:
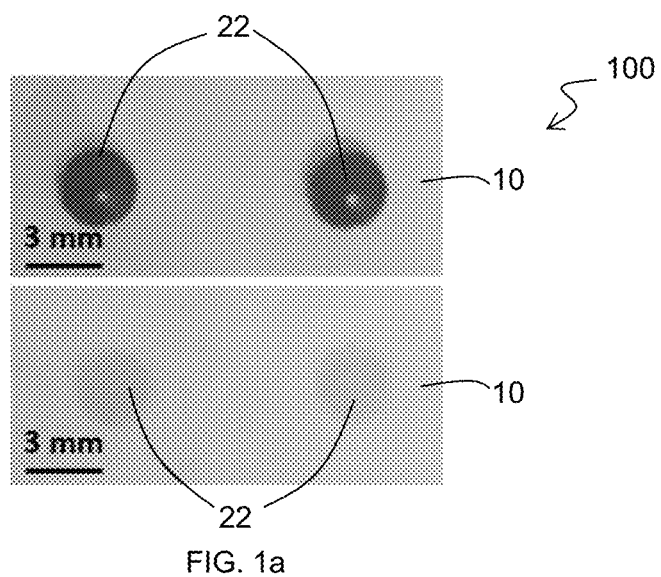
FIG. 1a is a photographic image of polydopamine deposited on a Teflon™-coated surface via a free-standing dopamine monomer droplet.

Exemplary embodiments of a digital magnetic microfluidic apparatus 100 and method of digital magnetic microfluidic manipulation will be described below with reference to FIGS. 1 to 14. The same reference numerals are used throughout the figures for the same or similar parts. Reference numerals relating to the method are indicated in brackets for ease of reference.

The digital magnetic microfluidic apparatus 100 comprises at least one hydrophilic surface energy trap 22 to retain liquid thereon, the surface energy trap 22 comprising a thin film or layer of polydopamine 22 formed on a hydrophobic surface 10. An exemplary embodiment of a hydrophobic surface comprises a Teflon™ surface 10 on a platform. The Teflon™ surface 10 may be provided as a Teflon™-coating on a substrate, or the platform itself may comprise a Teflon™ slab, for example. Where a Teflon™-coating is applied, the substrate may be made of another material, such as glass, for example. To create the hydrophilic thin film of polydopamine 22 on the hydrophobic Teflon™ surface 10 of the magnetic digital microfluidic apparatus 100, a polydopamine coating protocol was first optimized and the surface property after polydopamine modification was characterized using contact angle measurement.

The polydopamine may be deposited in situ on a Teflon™ surface 10 by polymerizing a dopamine monomer directly on the Teflon™ surface 10. The dopamine monomer may be provided in an alkaline solution. Dopamine monomers in the deposited solution spontaneously polymerize into polydopamine 22 that adheres strongly to the Teflon™ surface 10. Although the Teflon™ surface 10 was not wetted by the dopamine monomer solution, the polydopamine 22 formed is a result of the spontaneous polymerization could adhere to the Teflon™ surface 10 as evidenced by the emergence of a blackish or dark brown thin film 22 (FIG. 1a, top; FIG. 1d, top), a characteristic colour of polydopamine 22. Excess polydopamine may be rinsed away to leave a grey thin film of polydopamine 22 on the Teflon™ surface 10.

Specific regions of the Teflon™ surface 10 may be selectively patterned with polydopamine 22 by dispensing dopamine monomer solution as free-standing droplets on the Teflon™ surface 10. The dopamine monomer solution in the droplets spontaneously polymerized to form polydopamine 22 on the Teflon™ surface 10 (FIG. 1a, top), which resulted in circular polydopamine regions 22 formed on the surface 10 (FIG. 1a, bottom) after rinsing and drying to remove excess polydopamine. Using the free-standing droplet method, size of a circular deposited polydopamine spot 22 may be controlled by adjusting the volume of the monomer droplet. To determine the relationship between the size of the polydopamine surface energy trap 22 formed and the volume of the free-standing dopamine monomer solution droplet (also referred to as "monomer droplet") used to form the polydopamine surface energy trap 22, different volumes of 5 mg/ml of dopamine hydrochloride in 10 mM Tris buffer at pH 8.8 ranging from 1 to 50 μL were dispensed on a Teflon™-coated 10 glass coverslip and incubated for one hour at room temperature. After rinsing and drying, a picture of the coverslip and a reference ruler was taken, and the diameter of the polydopamine surface energy trap 22 was measured using ImageJ (National Institute of Health).

Figure 1B:
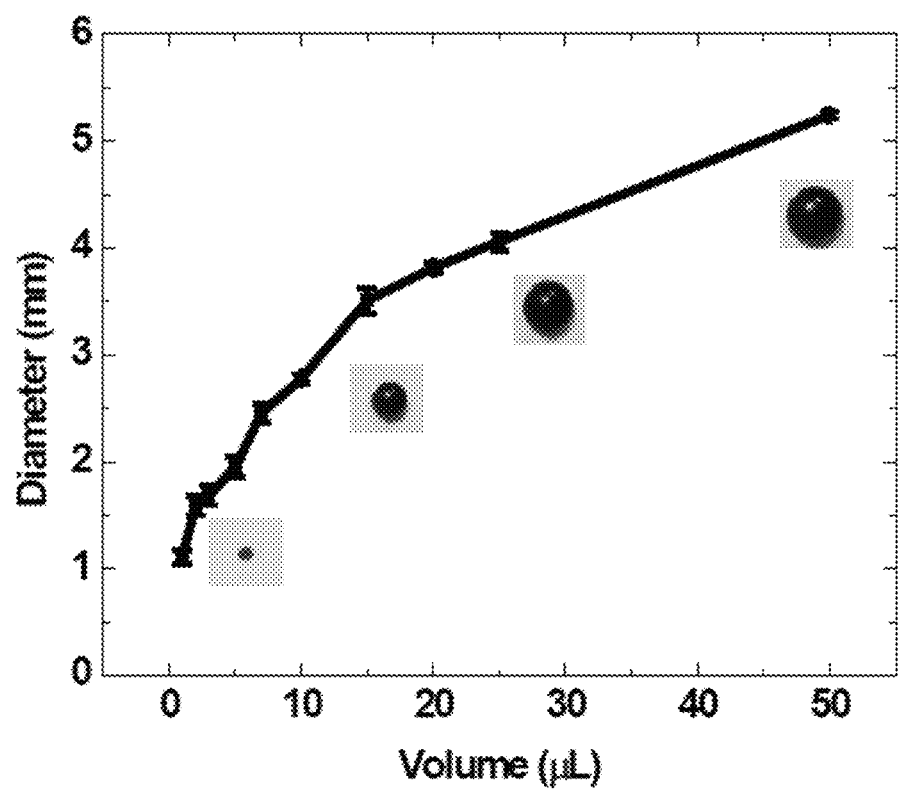
FIG. 1B is a graph of diameter of deposited polydopamine against volume of free-standing dopamine monomer droplet.
Figure 1C:
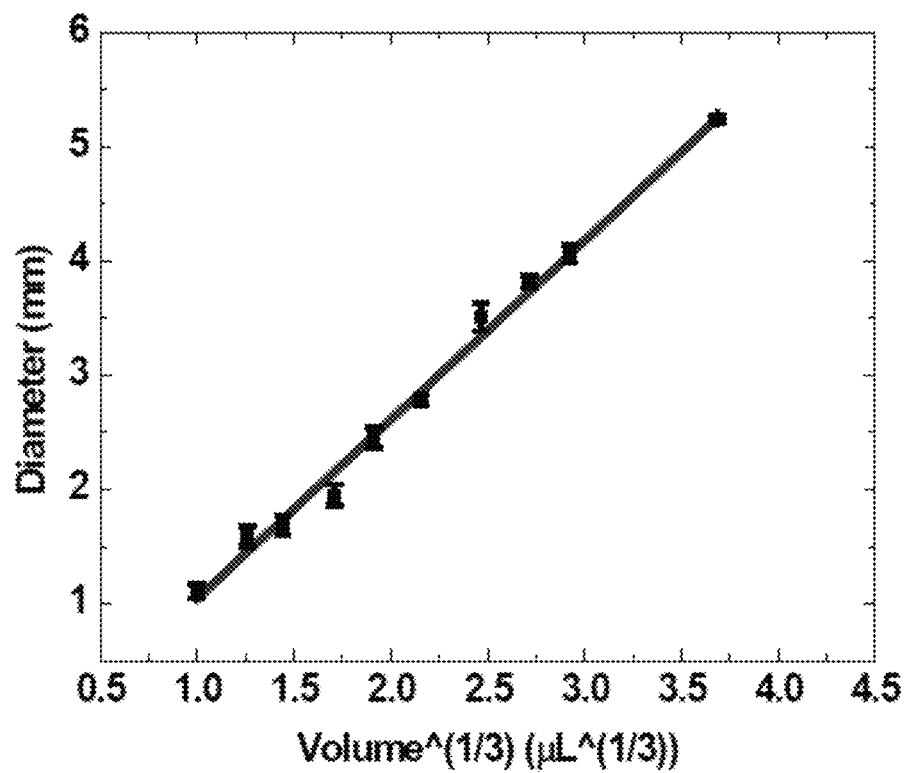
FIG. 1c is a graph of diameter of deposited polydopamine against cubic root of volume of free-standing dopamine monomer droplet.
Figure 1D:
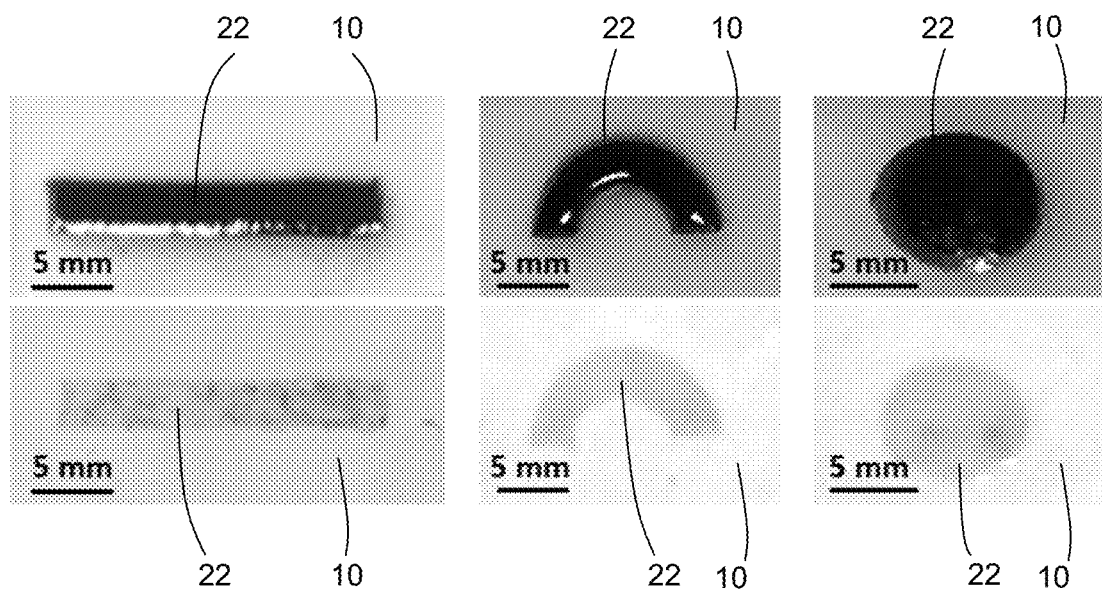
FIG. 1d is a photographic image of polydopamine deposited on a Teflon™-coated surface through stencils.

As shown in FIG. 1B, the diameter of the deposited polydopamine spot correlated positively correlated with the volume of the dopamine monomer solution, although the relationship was not linear. Instead, the diameter of the deposited polydopamine spot scaled linearly with a cube root of the monomer droplet volume (FIG. 1c). For monomer droplets having a diameter less than the capillary length (2.7 mm for water which corresponds to a monomer droplet of ~10 μL in volume), the shape of the monomer droplet is a spherical cap because the gravitational effect is negligible. As the volume of the monomer droplet increases, the effect of gravity starts to play a significant role in shaping the droplet. The large monomer droplets are no longer spherical in shape, but slightly flattened due to gravity. Therefore, it was seen that there was a linear relationship between the diameter of the deposited polydopamine spot and the cube root of the monomer droplet volume up to 50 μL, which suggests that the contact area between the monomer droplet and the Teflon™-coated surface is not strongly influenced by the shape of the monomer droplet under the influence of the gravity.

Alternatively, the surface energy trap 22 comprising a hydrophilic thin film of polydopamine 22 may be formed by exposing the Teflon™ surface 10 to the dopamine monomer solution through a stencil (not shown), which polymerized to form polydopamine 21 on the surface 10 (FIG. 1d, top), thereby allowing areas of any arbitrary shape to be patterned with a thin film of polydopamine 22 (FIG. 1d, bottom). For example, the stencil may be made of silicone rubber. In exemplary embodiments, either polydimethylsiloxane (PDMS) (Dow Corning Inc) or Dragon Skin® silicone was used to fabricate the stencil. The PDMS was prepared by mixing the polymer base and the crosslinker, and the dragon skin silicone was prepared according to manufacturer's instruction. The design of the stencil was realized by cutting and punching using manual tools and/or a laser cutter.

Using any of the above deposition embodiments, a hydrophilic surface energy trap 22 comprising a thin film of polydopamine 22 may thus be formed on a Teflon™ surface 10 by contacting a predetermined area of the Teflon™ surface 10 with an alkaline solution of dopamine monomer that spontaneously polymerizes to form a thin film of polydopamine 22 on the Teflon™ surface 10, the thin film of polydopamine 22 having a same size and shape as the predetermined area.

Polydopamine Characterization and Coating Condition Optimization

Figure 1E:
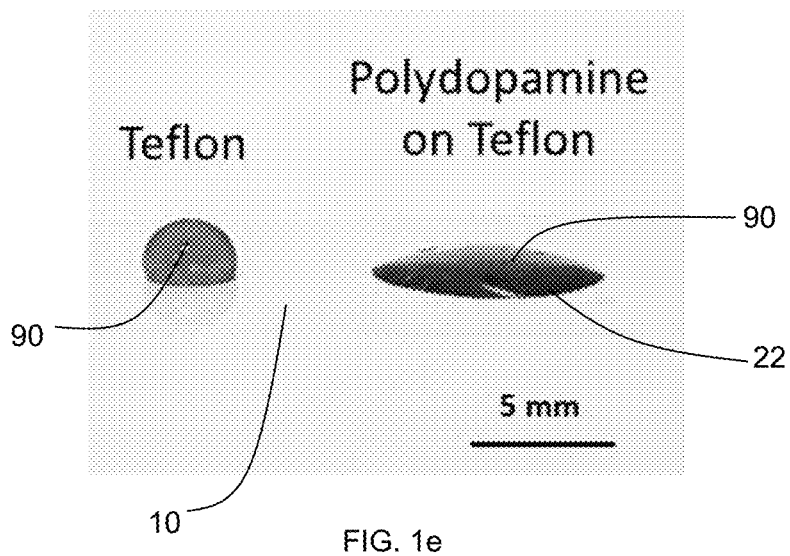
FIG. 1e is a photographic image of a droplet deposited on a Teflon™-coated surface and a droplet deposited on a polydopamine surface energy trap.
Figure 1F:
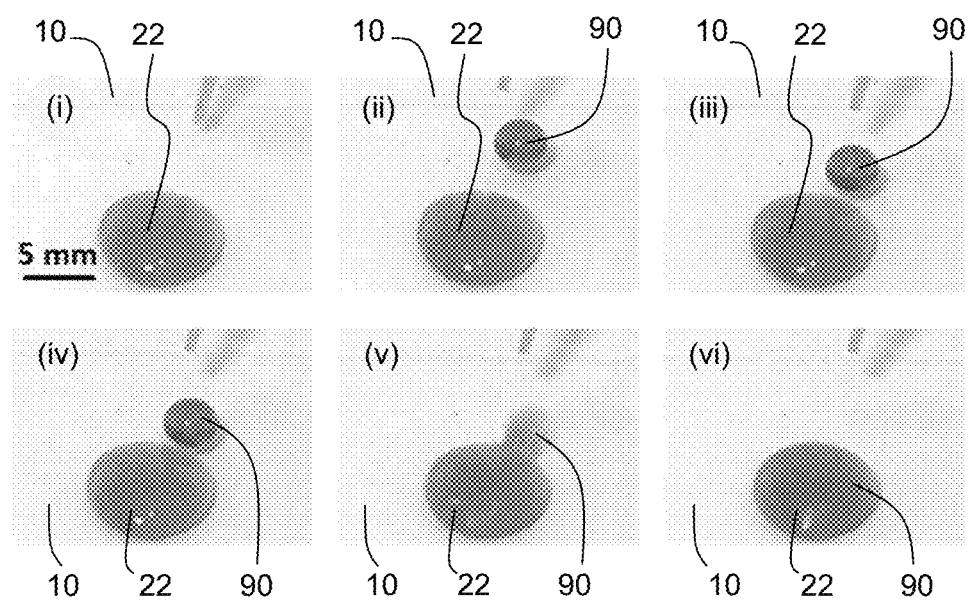
FIG. 1f is a series of photographic image of movement of a droplet over a Teflon™-coated surface onto a polydopamine surface energy trap.

As shown in FIG. 1e, when a liquid 90 is deposited on a Teflon™ surface 10, the liquid would form a droplet 90 with a large contact angle on the Teflon™ surface 10 (left image) due to the hydrophobic nature of the Teflon™-coated surface 10. But once the Teflon™ 10 was coated with a hydrophilic thin film of polydopamine 22, a liquid 90 deposited on the polydopamine thin film 22 would spread and result in a small contact angle (right image). Droplets 90 can thus move freely on the Teflon™-coated surface 10 but once the droplets 90 reached the polydopamine 22, the droplets 90 would be anchored by the polydopamine 22, as shown in FIG. 1f. Therefore, the effect on a liquid droplet of the polydopamine modification on the Teflon™-coated surface may be characterized by measuring the contact angle of the liquid droplet.

Figure 2A:
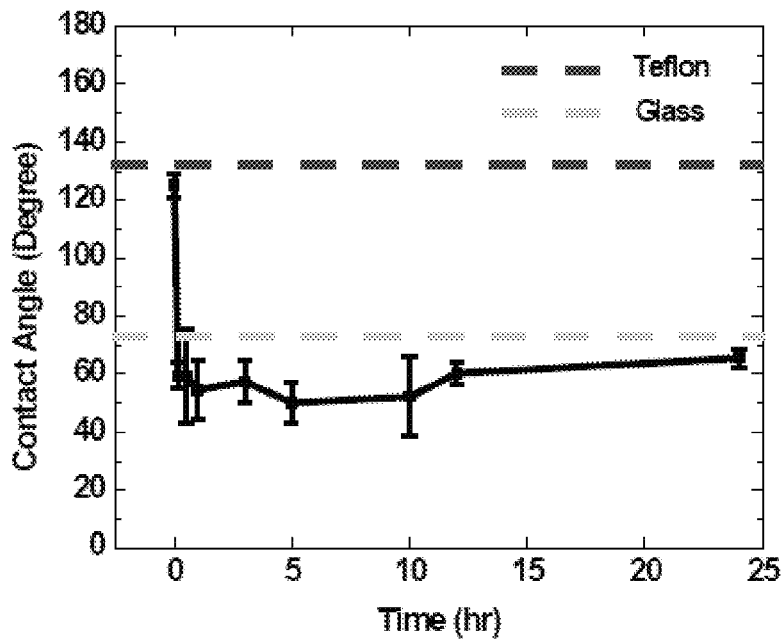
FIG. 2a is a graph of liquid droplet contact angle on polydopamine against incubation time of dopamine monomer solution when forming the polydopamine.

First, the reaction time for the polydopamine modification, i.e. the duration that the dopamine monomer solution was in contact with Teflon™-coated surface was optimized by incubating the Teflon™-coated surface with the dopamine monomer solution for various durations. For example, 30 μl of dopamine monomer solution with a concentration of 5 mg/ml in 10 mM Tris buffer at pH 8.8 was dispensed onto a Teflon™-coated glass coverslip and allowed to rest for various periods of time ranging from 0 minutes to 24 hours. After that, the glass coverslip was rinsed with deionized water, and the contact angle was measured. As shown in FIG. 2a, at time 0, the contact angle was above 120°. After a 10-minute incubation, the colour of the dopamine monomer solution started to turn dark, a characteristic sign of the formation of polydopamine. The polydopamine deposited on the Teflon™ reduced the contact angle to 60-70°, similar to that of a regular glass coverslip. As the incubation duration was further increased, no significant change in contact angle even up to 24 hours was observed (FIG. 2a). The contact angles measured at various time point within the 24-hour period all showed similar values ranging roughly between 50-70°. These results suggested that a long incubation period was unnecessary to create surface energy traps on the Teflon™-coated using polydopamine.

Figure 2B:
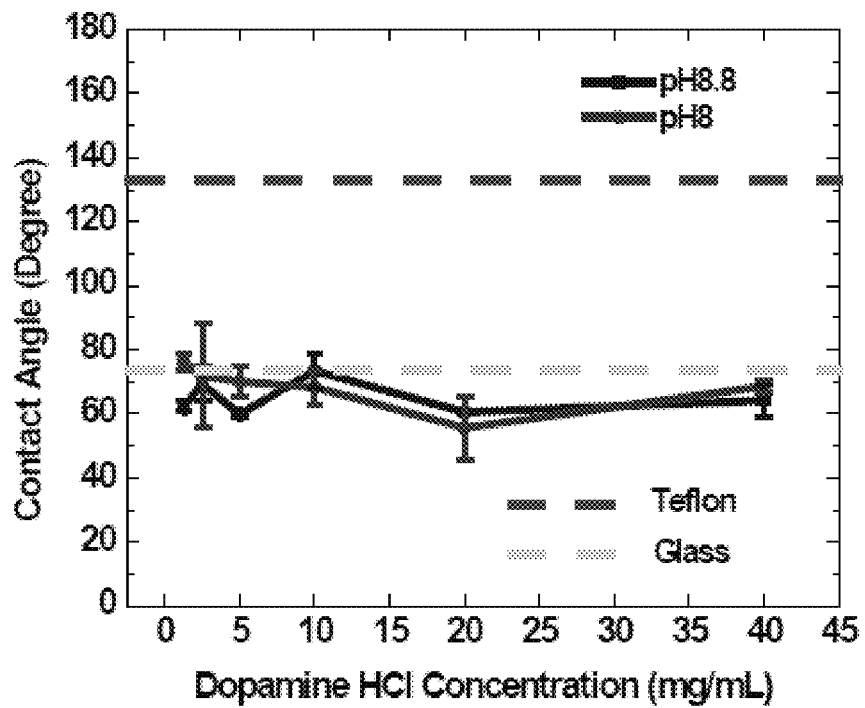
FIG. 2b is a graph of liquid droplet contact angle on polydopamine against dopamine HCl concentration and buffer pH used when forming the polydopamine.
Figure 3:
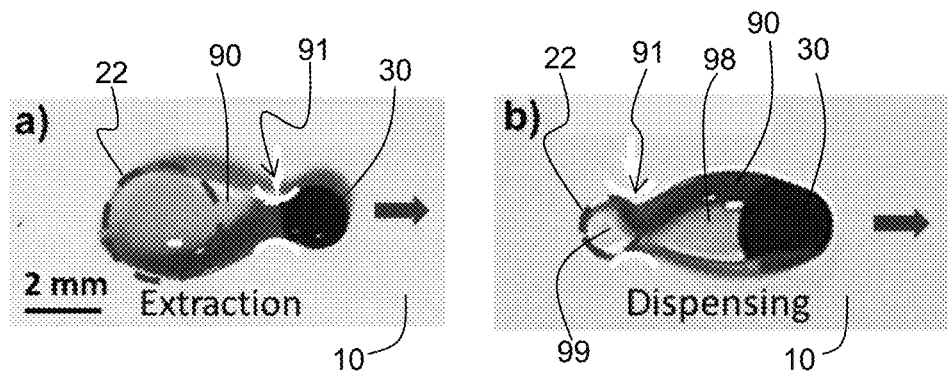
FIG. 3a is a photographic image showing formation of a necking point after moving a liquid droplet over a relatively big surface energy trap.
FIG. 3b is a photographic image showing formation of a necking point after moving a liquid droplet over a relatively small surface energy trap.

Next, the effect of buffer pH and dopamine monomer concentration on the polydopamine coating on the Teflon™-coated surface was tested. Using 2 mg/mL dopamine-HCl monomer solution in a buffer at pH 8.0, a polydopamine thin film was deposited on the Teflon™-coated surface with a contact angle of around 70°, similar to the contact angle of the glass coverslip. As the concentration of dopamine-HCl monomer increased up to 40 mg/mL, no significant change in contact angle was observed. The experiment was repeated with the Tris buffer at pH 8.8, and the same result was observed, i.e., no significant change in contact angle with increase in concentration of dopamine-HCl monomer (FIG. 2b). To perform these experiments, a piece of microscope coverslip of 24 mm×50 mm was first coated with 1% Teflon™ AF dissolved in Fluorinert FC-40 and baked at 75° C. for 10 minutes. Then, a serial dilution of dopamine monomer solution (Dopamine hydrochloride, Sigma-Aldrich) was performed, in which dopamine monomer solutions of different concentrations ranging from 1.25 to 40 mg/ml were dissolved in 10 mM Tris buffer of pH 8.0 and pH 8.8 (1st Base Technology) to obtain different concentrations of dopamine monomer solution in a buffer. Next, 30 μl of each concentration of dopamine monomer solution in a buffer was placed on a Teflon™-coated glass coverslip for one hour at room temperature, and the glass coverslip was subsequently washed with deionized water. The contact angle of each specimen was measured using a Theta auto wet angle machine with a water droplet having a volume of 5 μl.

The results above suggest that the characteristics of the polydopamine coating formed on the Teflon™-coat surface are not sensitive to the formation reaction conditions. Polydopamine coatings with similar wetting properties may be applied to a Teflon™-coated surface using various buffer conditions with a high tolerance for the reaction time and the dopamine monomer concentration. This property gives some leeway to create surface energy traps with consistent performance on the Teflon™-coated surface using the simple polydopamine coating protocol.

Another great advantage of polydopamine is that it forms a strong and long-lasting coating. Polydopamine is known for its strong adhesion to the substrate. It was found that the polydopamine-modified surface could retain wettability for several weeks to months. By comparison, a Teflon™-coated glass surface modified with oxygen plasma could only remain hydrophilic for several days at most.

Droplet Manipulation on Magnetic Digital Microfluidic Platform with Polydopamine Surface Energy Trap The regions deposited with polydopamine 22 on a Teflon™ surface 10 function as surface energy traps on the Teflon™ surface 10 by anchoring a liquid droplet on the polydopamine 22 with its high surface tension. On a magnetic digital microfluidic apparatus 100 having a platform 101 with a plain Teflon™-coated 10 substrate, a moving droplet experiences two main forces in the horizontal direction, a magnetic force provided by a magnet on magnetic particles added to the droplet and frictional force in a direction opposite to droplet movement. The net effect of the two forces and the surface tension surrounding the magnetic particles determines if the droplet would move together with the magnetic particles or if the magnetic particles would split from or leave the droplet. In conventional magnetic digital microfluidic platforms, the extraction of magnetic particles can be accomplished only by increasing the moving speed. Nevertheless, in certain bioassays, the quantity of magnetic particles required is too large to break the surface tension and leave the droplet at any feasible moving speed.

To control the motion of a liquid droplet on a platform of a digital magnetic platform, an external magnetic force is applied via an external magnetic field to drive the magnetic particles. Due to the surface tension of the liquid droplet, the magnetic particle cluster in the droplet cannot easily break away from the droplet. As a result, the magnetic particles would move together with the droplet. At a constant moving speed, the magnetic force is balanced by the frictional force that is proportional to the speed. As the speed is increased, the magnetic force required to balance the frictional force is also increased. At a critical point, the magnetic force acting on the droplet would be large enough for the magnetic particle cluster to break the surface tension, causing the magnetic particles to split from or leave the droplet. Because the break-away speed required could be unfeasibly high under certain assay conditions, the presently disclosed surface energy trap comprising a thin film of polydopamine is introduced to provide an additional force in the opposite direction of the movement to facilitate the magnetic particle extraction process.

As shown in FIG. 3a, once the droplet 90 was moved over or onto a large polydopamine surface energy trap 22, the surface energy trap 22 immobilized the droplet 90 while the magnetic particle cluster 30 continued to move, leading to the formation of a necking point 91 between the droplet 90 and the magnetic particle cluster 30. As the magnetic particle cluster 30 moved further away, the curvature at the necking point 91 gradually increased until the Laplacian pressure caused breakage at the necking point 91 resulting in particle 30 extraction from the droplet 90.

In another scenario, as shown in FIG. 3b, the magnetic particle cluster 30 moved over a small surface energy trap 22, and a necking point 91 was formed between the droplet 90 and the surface energy trap 22. Once the necking point 91 broke, a small portion or daughter droplet 99 of the droplet 90 was withheld within the surface energy trap 22 while the rest 98 of the droplet 90 continued moving with the magnetic particles 30, resulting in passive liquid dispensing.

In general, as a droplet 90 is being dragged over a surface energy trap by a cluster of magnetic particles, two necking points 91 could potentially form, a first necking point 91 between the droplet 90 and the surface energy trap 22, and a second necking point 91 between the droplet 90 and the magnetic particle cluster 30. Under certain scenarios, one of the two necking points 91 would break before the other one is fully developed, like the ones shown in FIGS. 3a and 3b.

From the above description, it can be understood that a present method of magnetic digital microfluidic manipulation comprises the basic steps of: contacting a liquid droplet containing magnetic particles with a polydopamine surface energy trap on a hydrophobic surface; retaining at least a portion of the liquid droplet on the surface energy trap; and moving at least the magnetic particles with a magnetic force. For particle extraction, all of the liquid droplet is retained by the surface energy trap and only the magnetic particles are moved by the magnetic force out of the liquid droplet. For dispensing, only a portion of the liquid droplet is retained on the surface energy trap while the remainder of the droplet and the magnetic particles are moved away from the surface energy trap.

Figure 4:
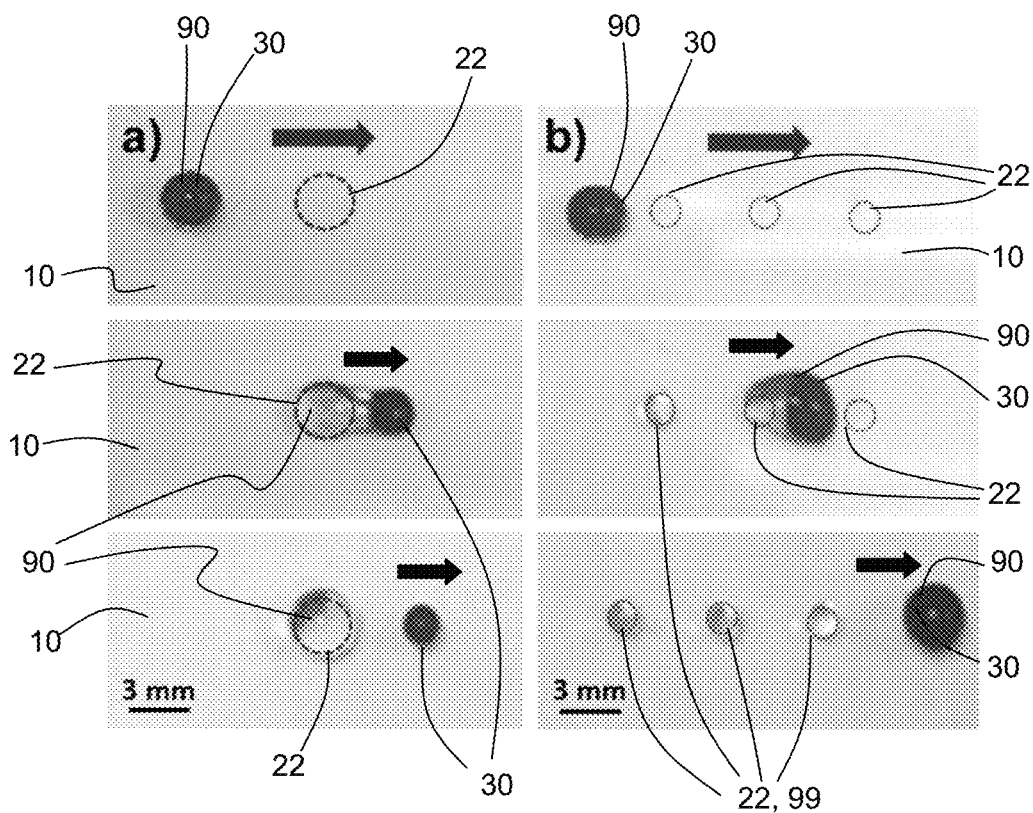
FIG. 4a is a photographic image showing extraction of magnetic particles from a liquid droplet.
FIG. 4b is a photographic image showing liquid dispensing from liquid droplet.
Figure 5A:
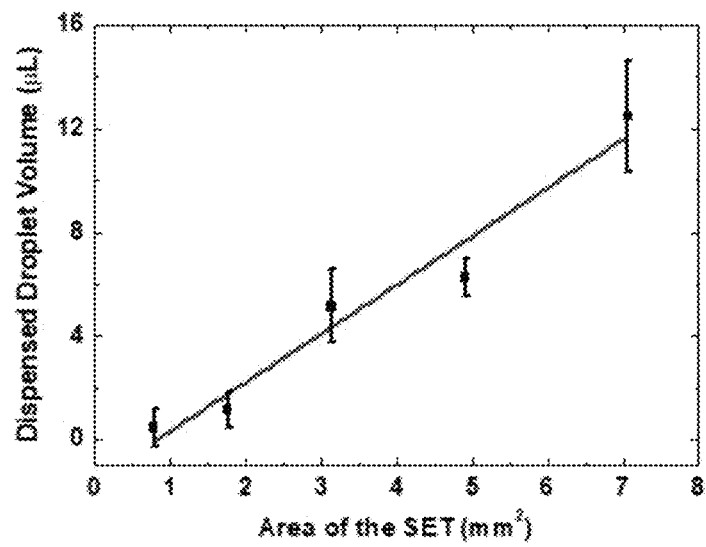
FIG. 5a is a graph of volume of dispensed liquid droplets against area of surface energy trap.

Using the above described mechanisms, various types of droplet manipulation on a polydopamine-enabled platform of a magnetic digital microfluidics apparatus was demonstrated using food colouring to dye liquid droplets that were moved over thin films of polydopamine 22 deposited on a Teflon™ surface 10, as shown in FIGS. 4 to 6, in which circular surface energy traps were fabricated using the free-standing droplet method and surface energy traps of other shapes were fabricating using a stencil, as described above. By moving a 10 µL droplet 90 with 2 µl of magnetic particles 30 (MagAttract® Suspension G from Qiagen) over a large surface energy trap 22 (FIG. 4a) of about 3 mm in diameter, magnetic particles 30 could be easily extracted from the droplet 90 that is retained by the surface energy trap 22. Multiple aliquots could also be dispensed by splitting small droplets from a 10-µl parent droplet 90 using a series of small surface energy traps 22 (FIG. 4b) of about 1.5 mm in diameter. The volume of the droplet dispensed using the surface energy trap is proportional to the area of the surface energy trap, as shown in FIG. 5a. The smallest surface energy trap studied was 1 mm in diameter or 0.78 mm² in area, which allows the dispensing of a daughter droplet of ~470 nL in volume. With a surface energy trap of 3.5 mm in diameter or 7.07 mm² in area, a daughter droplet of 12.5 µL in volume could be dispensed. Surface energy traps greater than 3.5 mm would often lead to particle extraction.

Figure 5B:
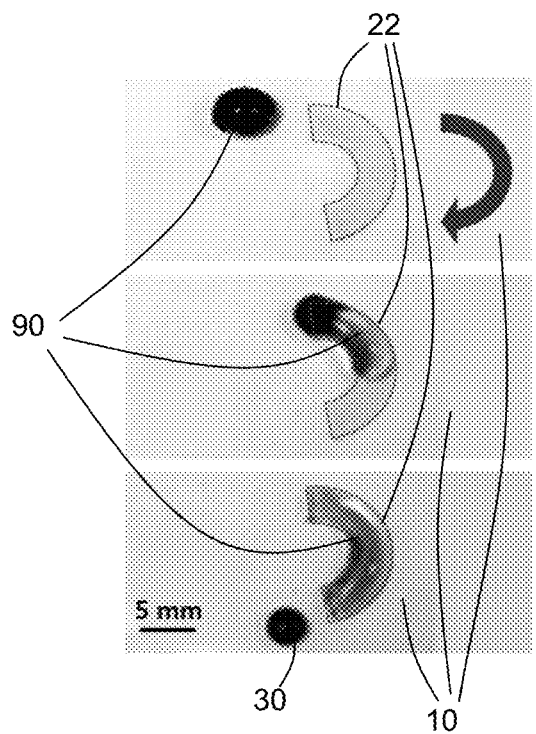
FIG. 5b is a photographic image showing shaping of a liquid droplet.

Because the polydopamine surface energy trap 22 is the only wettable region on the Teflon™-coated substrate, polydopamine modification could be used for fluid shaping to shape the liquid droplet (FIG. 5b). This was achieved by first patterning or depositing a crescent-shaped region or film of polydopamine 22 through a silicone stencil. As a 15-µL droplet 90 was dragged over the polydopamine surface energy trap 22, the droplet 90 wet the entire polydopamine-coated area 22 and was shaped into the crescent as it was retained by the polydopamine 22. Thus, a shape of the liquid droplet 90 retained by the surface energy trap 22 conforms with the shape of the surface energy trap 22.

Figure 5C:
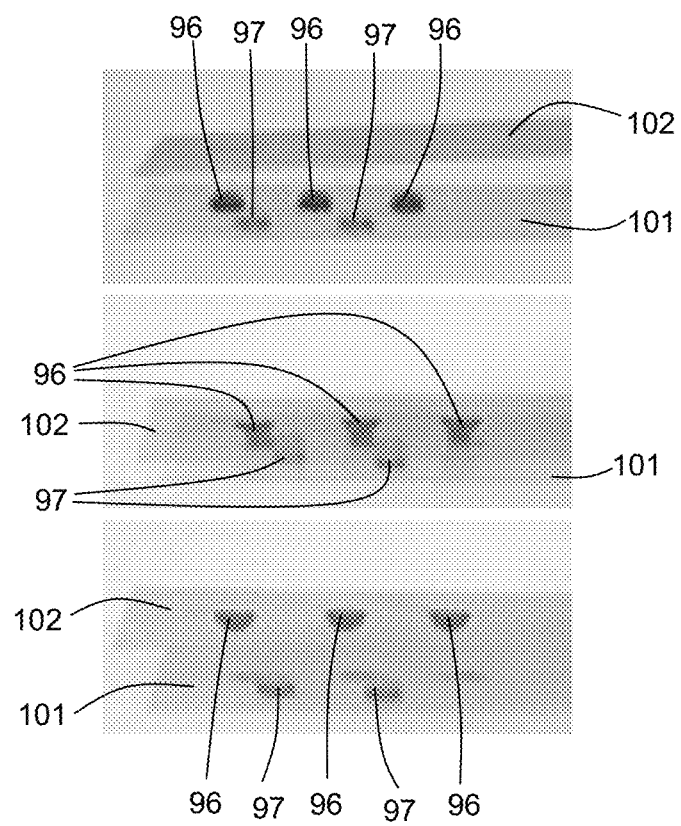
FIG. 5c is a photographic image showing liquid droplet transfer from a first platform to a second platform.
Figure 6A:
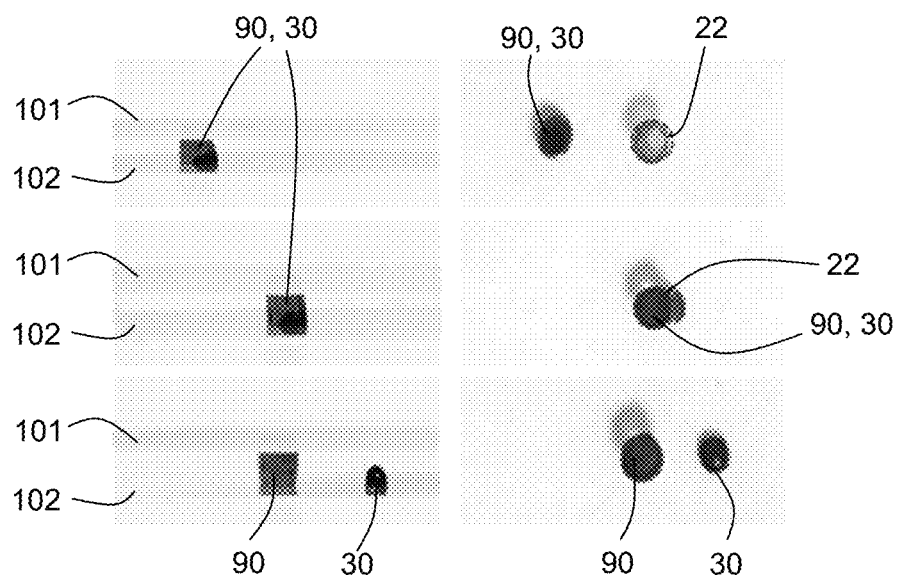
FIG. 6a is a photographic image showing side and top views of extraction of magnetic particles from a liquid droplet in a two-plate configuration.
Figure 6B:
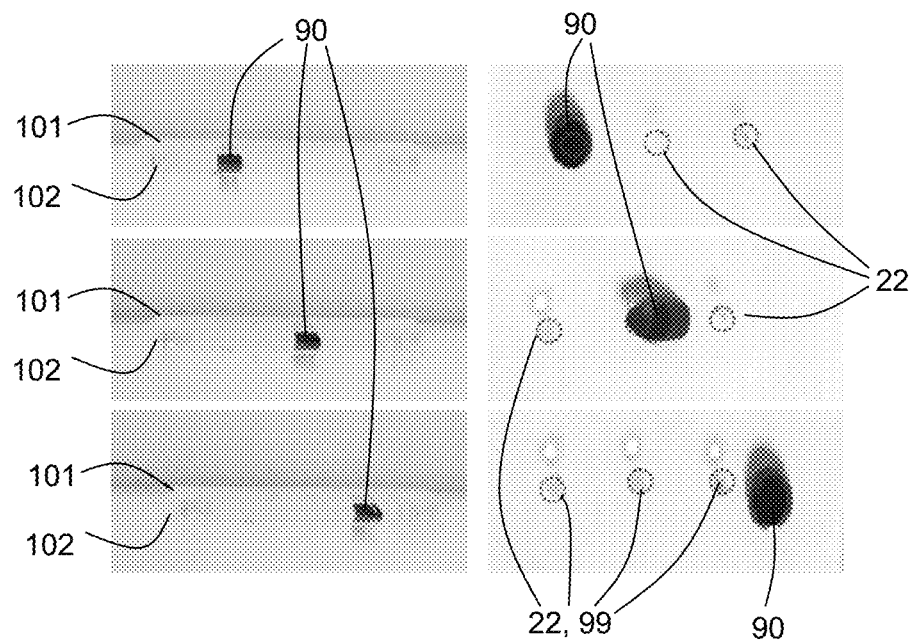
FIG. 6b is a photographic image showing side and top views of liquid dispensing from a liquid droplet in a two-plate configuration.
Figure 6C:
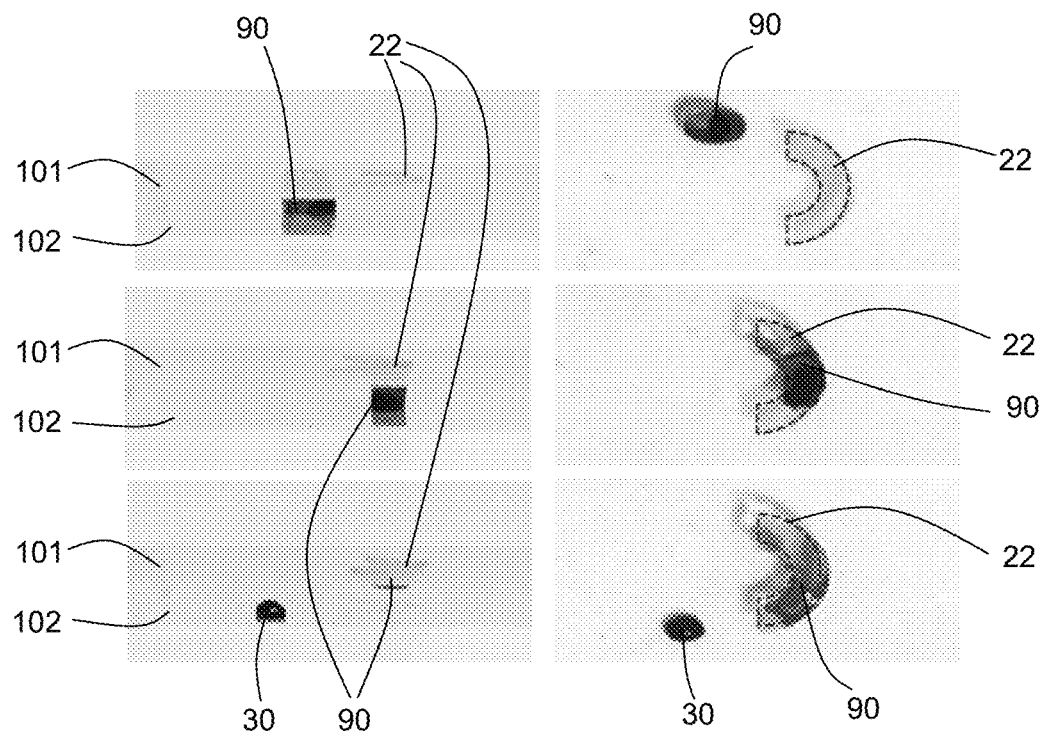
FIG. 6c is a photographic image showing side and top views of shaping of a liquid droplet in a two-plate configuration.

The adhesive force provided by the polydopamine 22 also enables selective transfer of droplets from one platform to another. As shown in FIG. 5c, three green droplets 96 and two orange droplets 97, 10 µL each, were placed on a Teflon™-coated substrate forming a first platform 101. On another Teflon™-coated platform 102, three surface energy traps (not visible) were created using 10-µl free standing droplets of dopamine-HCl. As the two platforms 101, 102 were brought close to one another so that the second platform 102 came into contact with the green droplets 96 as well as the orange droplets 97, the surface energy traps on the second platform 102 that were positioned over the green droplets 96 caught the green droplets 96 and lifted them up. As a result, the green droplets 96 were selectively transferred from the first platform 101 to the second platform 102, but the orange droplets 97 were not transferred as the orange droplets did not adhere to the Teflon™ surface 10 of the second platform 102. This droplet operation can thus be used to transfer samples between different magnetic digital microfluidic platforms for multi-stage analysis.

The demonstrations shown in FIGS. 4 and 5 were performed on a single-plate configuration, which is typical for magnetic digital microfluidics. However, EWOD-based digital microfluidics often uses a two-plate configuration by sandwiching the droplet between two Teflon™-coated coverslips. Accordingly droplet manipulation using polydopamine surface energy traps 22 in a two-plate configuration of the magnetic digital microfluidic apparatus 100 was also studied, as described below with reference to FIGS. 6a to 6c. In this demonstration, the droplets 90 were placed between and in contact with two coverslips 101, 102, and the polydopamine surface energy trap 22 was fabricated on the top glass coverslip 102. As the droplet 90 moved over the surface energy trap 22, the droplet 90 was pinned to the top glass coverslip 102 at the polydopamine film 22 whereas the magnetic particles 30 continued moving on the bottom glass coverslip 101. Particle extraction (FIG. 5a), liquid dispensing (FIG. 5b) and liquid shaping (FIG. 5c) using the two-plate configuration were demonstrated using the same operation conditions as the single-plate configuration described above with reference to FIGS. 4a to 4c.

In the single-plate configuration, a minute number of magnetic particles 30 were observed to be occasionally stuck at the surface energy trap 22. This situation was more frequent with large surface energy traps where the magnetic particles 30 needed to travel a greater distance over the sticky polydopamine region 22, as in the case with the fluid shaping (FIG. 4c). In contrast, in the two-plate configuration, the magnetic particles 30 were pulled down to the bottom coverslip by the magnetic force. Consequently, the magnetic particles 30 were not in direct contact with polydopamine 22, and no particle was left behind after passing through the surface energy traps 22. However, the two-plate configuration is comparatively more difficult to assemble than the single-plate configuration, and the volume of the droplet that can be handled by the two-plate configuration is considerably smaller, which might make the two-plate configuration not suitable for certain bioassays.

Figure 7A:
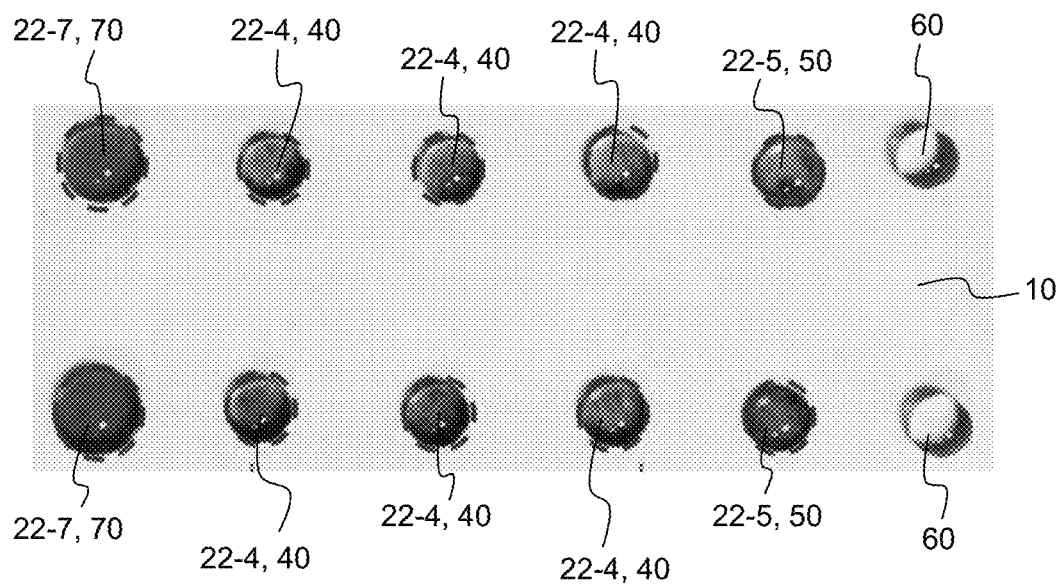
FIG. 7a is photographic image of liquid droplets provided on polydopamine surface energy traps formed on a hydrophobic surface for detection of hepatitis B surface antigen (HBsAg).
Figure 7B:
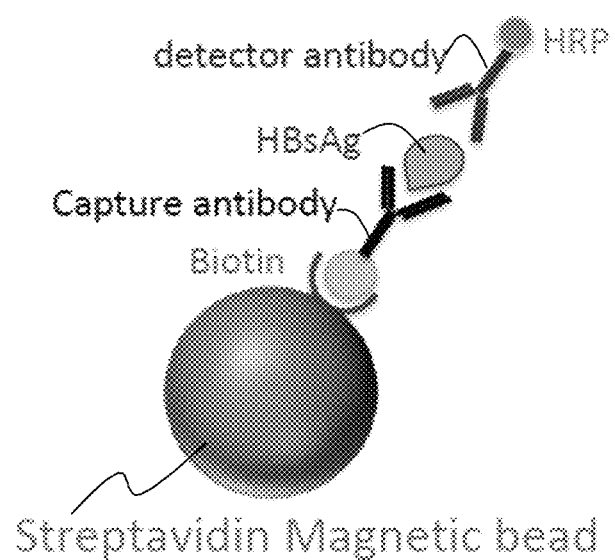

HBsAg by ELISA on Magnetic Digital Microfluidic Platform with Surface Energy Traps As an example of use, detection of hepatitis B surface antigen (HBsAg) on a platform of a magnetic digital microfluidic apparatus comprising polydopamine surface energy traps 22 on a Teflon™ surface 10 was demonstrated as potential point-of-care diagnostics of Hepatitis B. Hepatitis B is a serious disease affecting over 300 million people all over the world. The HBsAg is a well-recognized earlier diagnostic marker, and the level of HBsAg in serum serves as a good indicator of viral activity. To detect HBsAg, a standard curve was generated using ELISA (FIG. 7) on the magnetic digital microfluidic platform. To do so, the platform was first prepared and formed with two rows of polydopamine surface energy traps 22-7, 22-4, 22-5 as shown in FIG. 7a. To fabricate each row of polydopamine surface energy traps 22-7, 22-4, 22-5, four 10-µl and one 20-µl droplets of dopamine monomer solution were dispensed on a Teflon™-coated 10 coverslip at designated locations as shown in FIG. 7a and allowed to rest for 1 hour. For each row, the first surface energy trap 22-7 fabricated with 20 µL of dopamine monomer solution was around 3.5 mm in diameter, and the second to fifth surface energy traps 22-4, 22-5 fabricated with 10 µl of dopamine monomer solution were around 2.5 mm in diameter. After dopamine polymerization, the coverslip was rinsed with deionized water, dried and stored until use.

To prime the platform for ELISA, three 10-0 washing buffer droplets 40 (1×PBS with 0.1% (v/v) Tween™ 20 (Bio-Rad Inc.)) were dispensed on the second to fourth surface energy traps 24, one 10-µl 3,3',5,5'-Tetramethylbenzidine (TMB) droplet 50 (1-step ultra TMB solution from Thermo Fisher Scientific Inc.) was dispensed on the fifth surface energy trap, and one 10-µl stopping solution 60 (0.18 M H2SO4) was dispensed directly on the Teflon™ surface 10 next to the TMB droplet 50, as shown in FIG. 7a. All except the stopping solution droplet 60 were dispensed directly on the polydopamine surface energy traps 22-7, 22-4, 22-5 which would pin down the droplets 40, 50 to facilitate particle extraction and prevent undesired droplet movement during the washing process. To prevent evaporation during the relatively long incubation period, all samples 70 were incubated in a humidity-controlled environment. The stopping solution droplet 60 would be moved to merge with the TMB droplet 50 in the last step, so it was not confined by the surface energy trap 22.

Next, a twofold serial dilution of a sample containing 0 to 5 ng of HBsAg was mixed with magnetic particles (such as Dynabeads®) conjugated with a capture antibody for HBsAg and horseradish peroxidase (HRP)-labeled detector antibody in the sample droplet 70 that contained 5% bovine serum albumin as the dynamic blocking agent. To conjugate the Dynabeads®, firstly, 100 µl of 100 µg/ml monoclonal capture antibody (Monoclonal antibody, Zika virus (mouse), #10-2708, Achema) was conjugated with biotin using a biotin conjugation kit (Type B, Abcam Inc.). The biotin-conjugated capture antibody was incubated with 100 µl of 100 µg/ml streptavidin Dynabeads® (Dynabeads M-280 Streptavidin, Invitrogen) for an hour at room temperature. After incubation, the capture antibody bound to the magnetic Dynabeads® through biotin-streptavidin interactions. The antibody-conjugated Dynabeads® were washed three times and resuspended in 100 µl 1× Phosphate-buffered saline (PBS) (Vivantis Technology). Secondly, the monoclonal detector antibody was labeled with HRP using the HRP conjugation kit (Abcam) according to manufacturer's instructions. The labeled detector antibody was diluted to 10 ng/mL with 1×PBS+5% bovine serum albumin (BSA, Sigma-Aldrich Inc.).

Figure 7C:
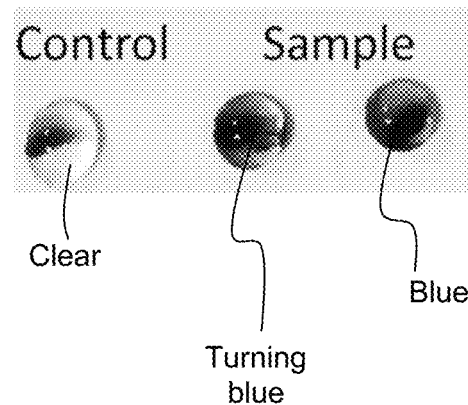
FIG. 7c is a photographic image of a control droplet remaining clear and sample droplets turning blue to indicate presence of HBsAg captured by the magnetic beads of FIG. 7b.
Figure 7D:
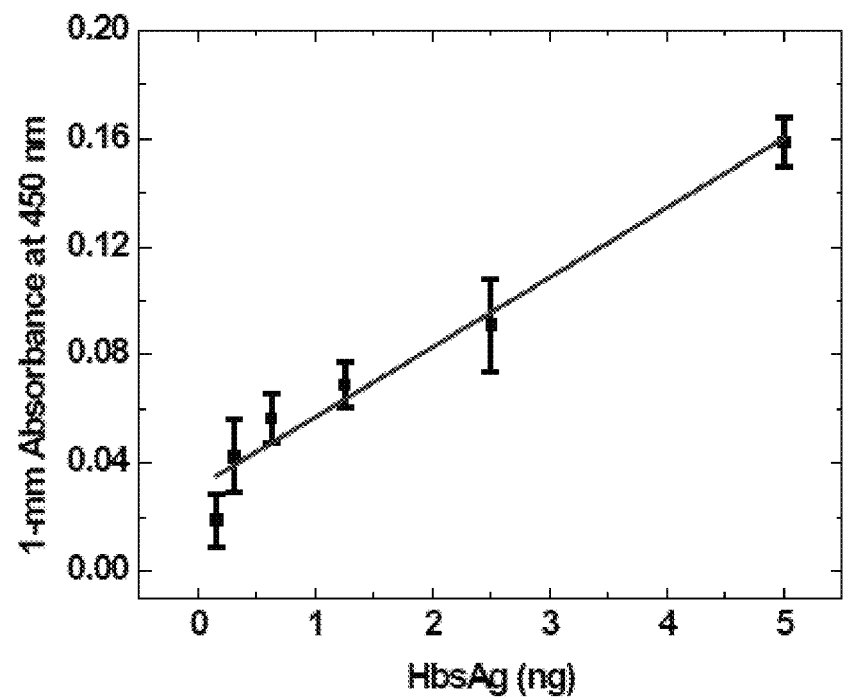
FIG. 7d is a graph showing absorbance values of developed TMB at 450 nm against HBsAg quantity.

After a one-hour incubation of the sample mixed with conjugated Dynabeads® at room temperature on the surface energy trap 22-7, the antibodies and the target HBsAg protein formed a sandwich structure immobilized on the surface of the magnetic particle (FIG. 7b) and the magnetic particles in the sample droplet 70 were extracted from the sample droplet 70 with the assistance of the polydopamine surface energy trap 22 by moving the Dynabeads® out from the sample droplet 70 using a permanent magnet while the sample droplets 70 was pinned down by the surface energy trap 22-7. Washing was accomplished by moving the Dynabeads® through the three washing buffer droplets 40 one at a time to eliminate any possible carryover contamination. During the washing step, all the washing buffer droplets 40 were anchored to the polydopamine surface energy traps 22-4 to facilitate magnetic particle extraction. After washing, the magnetic particles 30 with the antibody-antigen sandwich on their surfaces were merged with the TMB droplet 50 and incubated for 15 minutes. During the incubation, the color of the TMB gradually changed from clear to blue (FIG. 7c). In comparison, the negative control sample would not cause any color change, and the TMB droplet 50 would remain clear. After the incubation, the magnetic particles were removed from the TMB droplet 50 and merged with the stopping solution droplet 60. This was accomplished by using the Dynabeads® as actuators to bring the stopping solution droplet 60 to merge with the TMB droplet 50, in which the magnetic particles drove the stopping solution droplet 60 towards the TMB droplet 70. After the two droplets 50, 60 were merged, the two solutions were mixed by moving the Dynabeads® back and forth in the combined droplet, where the solution turned yellow and the enzymatic reaction stopped. The 450-nm absorbance of the developed TMB was measured using a mini UV-Vis spectrometer (BioDrop™). The absorbance values were plotted against the HBsAg quantity to generate the standard curve (FIG. 7d).

The limit of detection was calculated to be 67.1 ng/mL based on the linear regression. Studies showed that the hepatitis B patient's serum samples contained more than 1000 IU/mL, or roughly 430-580 ng/mL depending on the conversion standard of HBsAg. As a result, the serum samples can be used directly without the need for dilution. The same ELISA assay was performed using a conventional 96-well microplate. The linear range obtained on the present magnetic digital microfluidic platform agreed with the control experiment done using the conventional 96-well plate and with the reported range (0.5 to 1 ng/mL) in the literature. Although the limit of detection is lower for the conventional ELISA, the input sample volume was 10 times larger than the droplet-based ELISA on the magnetic digital microfluidic platform. Furthermore, the microplate-based ELISA could not use the serum sample directly, sample dilution was required to match the HBsAg concentration with the linear range.

The above description presents a novel method of creating surface energy traps to facilitate droplet manipulations on the magnetic digital microfluidic platform using the mussel-inspired polydopamine. The unique ability of polydopamine to strongly adhere to the otherwise non-wettable Teflon™ enables patterning of hydrophilic regions on the hydrophobic Teflon™ surface with great ease. The reaction conditions for coating polydopamine on Teflon™ was optimized in terms of dopamine monomer concentration, buffer pH, and reaction time, and characterized the polydopamine coating on Teflon™ by measuring the contact angle. The shape and size of the polydopamine surface energy traps are controlled by adjusting the volume of dopamine monomer solution or using a silicone stencil. Using the polydopamine surface energy traps, a wide range of droplet operations were demonstrated, including particle extraction, liquid dispensing, liquid shaping and cross-platform transfer on the magnetic digital microfluidic platform. Surface energy trap-assisted droplet manipulation using the two-plate format on the magnetic digital microfluidic platform was demonstrated, as well as protein quantification in multiplicate. Also demonstrated was the detection of HBsAg using an ELISA assay on the polydopamine surface energy trap-assisted magnetic digital microfluidic platform for potential point-of-care diagnostics of hepatitis B infection.

To further facilitate droplet manipulation, the magnetic digital microfluidic apparatus 100 may include at least one droplet manipulator 80 that is configured to perform a specific function, as shown in FIGS. 8a to 13. A surface energy trap 22 of the magnetic digital microfluidic apparatus 100 may be provided on the droplet manipulator 80. In exemplary embodiments, the surface energy trap 22 on the droplet manipulator 80 may be formed by dip-coating the droplet manipulator with 5 mg/ml of dopamine solution for an hour followed by drying at room temperature. Providing a surface energy trap 22 on a droplet manipulator 80 allows configuration of the droplet manipulator 80 to function as a magnetic particle extractor 80E or as a liquid dispenser 80D, for example, as will be described in greater detail below. The droplet manipulator 80 may be configured to be releasably attachable to a platform 101 of the apparatus 100, preferably at any one of a plurality of selectable locations on the platform 101. In this way, the apparatus 100 can be selectively configured to perform different functions by attaching an appropriate droplet manipulator 80 to the platform 101 to perform the specific function provided by the attached droplet manipulator 80. Alternatively (not shown), the droplet manipulator 80 may be provided at a predetermined location on the platform 101. By providing multiple droplets manipulators 80 that are configured to perform different functions (e.g. particle extraction 80E, liquid dispensing 80D, mixing 80M) on the platform 101 as shown in FIGS. 8a to 7c, the magnetic digital microfluidic apparatus 100 can be configured to perform multiple different droplet manipulation functions.

Figure 9B:
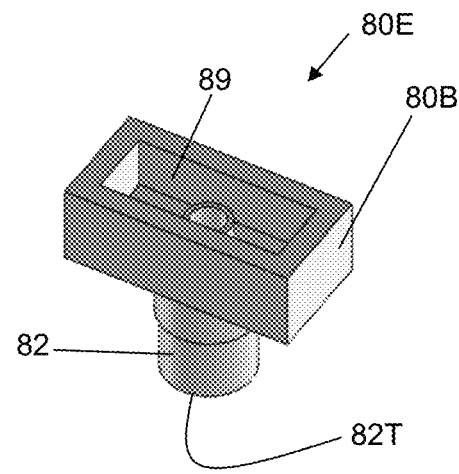
Figure 9C:
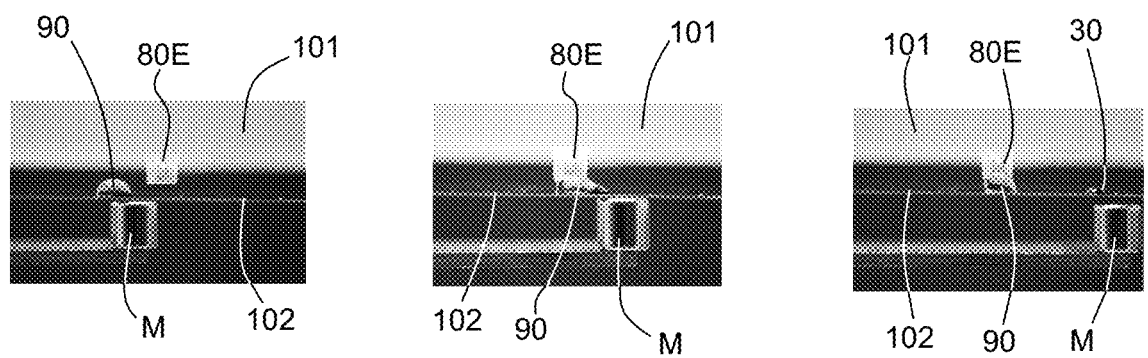
FIG. 9c is a series of photographic images of a side view of the droplet manipulator of FIG. 9a being used to extract magnetic particles from a liquid droplet.

For example, a magnetic-particle extracting embodiment 80E of the droplet manipulator 80 as shown in FIGS. 9a and 9b may comprise a projection 82 having a C-shaped cross-section that has a hydrophobic surface 10. The hydrophobic surface 10 may be formed by dip-coating the droplet manipulator 80 with 1% Teflon™ for an hour followed by drying at room temperature. A tip 82T of the projection 82 is coated with polydopamine to form a surface energy trap 22 at the tip 82T of the projection 82 of the droplet manipulator 80. When the droplet manipulator 80E is attached to the platform 101 and arranged such that the projecting tip 82T is facing downwards, as shown in FIG. 8a and FIG. 9b, the droplet manipulator 80E functions as a magnetic particle extractor when a liquid droplet 90 (exemplary volume of 10 μl) containing magnetic particles (for example 7 μl of MagAttract® Suspension G magnetic particles from Qiagen) and provided on a hydrophobic surface 102 is contacted with the surface energy trap 22 of the droplet manipulator 80E. All of the liquid droplet 90 is retained by the surface energy trap 22 at the C-shaped tip 82T while the magnetic particles 30 are moved out of the retained liquid droplet 90 by the magnetic force provided by the magnet M.

Figure 10A:
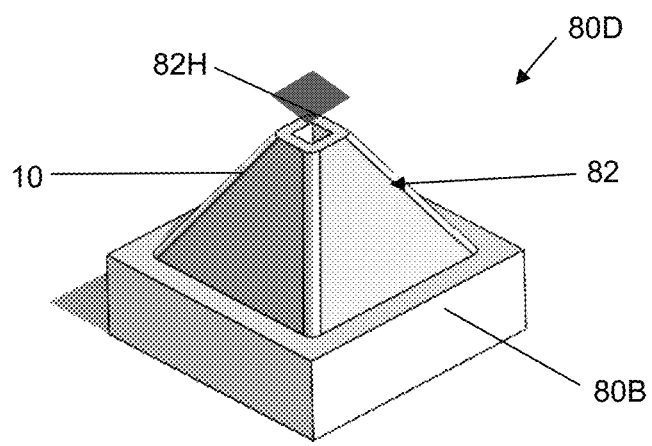
FIG. 10a is a bottom perspective view of a droplet manipulator configured to facilitate liquid dispensing from a liquid droplet.
Figure 10B:
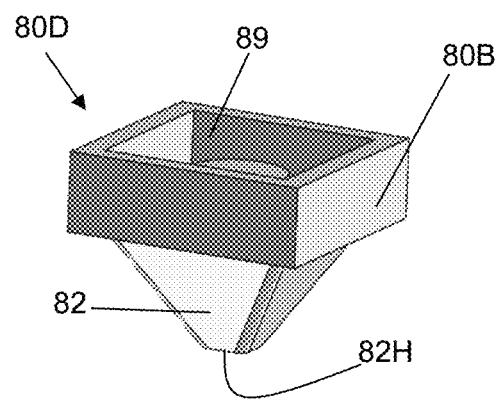
Figure 10C:
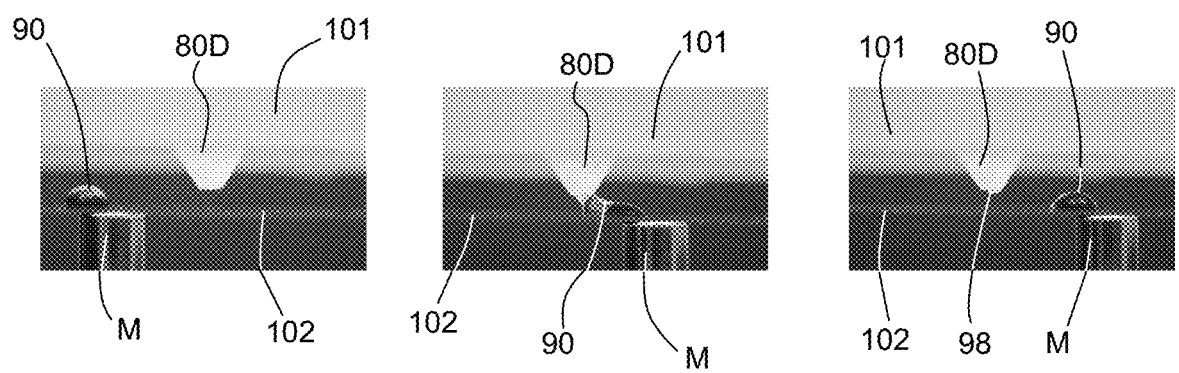
FIG. 10c is a series of photographic images of a side view of the droplet manipulator of FIG. 10a being used to dispense liquid from a liquid droplet.

In another example, a liquid dispensing embodiment 80D of the droplet manipulator 80 as shown in FIGS. 10a and 10b may comprise a projection 82 having a hole 82H provided at a tip of the projection 82. The hole 82H may be a blind hole or a through hole. The projection 82 may have a hydrophobic surface 10 formed by dip-coating the droplet manipulator 80 with 1% Teflon™ for an hour followed by drying at room temperature. The hole 82H is coated with polydopamine to form a surface energy trap 22 at the hole 82H. When the droplet manipulator 80D is attached to the platform 101 and arranged such that the hole 82H is facing downwards, as shown in FIG. 8a and FIG. 10b, the droplet manipulator 80D functions as a liquid dispenser when a liquid droplet 90 containing magnetic particles and provided on a hydrophobic surface 102 is contacted with the surface energy trap 22 of the droplet manipulator 80D. A portion of the liquid droplet 90 is retained by the surface energy trap 22 in the hole 82H while the magnetic particles 30 as well as the rest of the liquid droplet 90 are moved away by the magnetic force provided by the magnet M.

Figure 11:
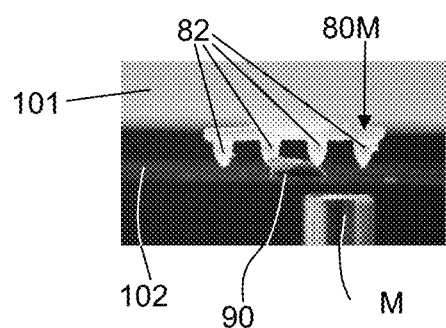
FIG. 11 is a photographic image of a side view of a droplet manipulator configured to facilitate mixing in a liquid droplet during use of the droplet manipulator.
Figure 12:
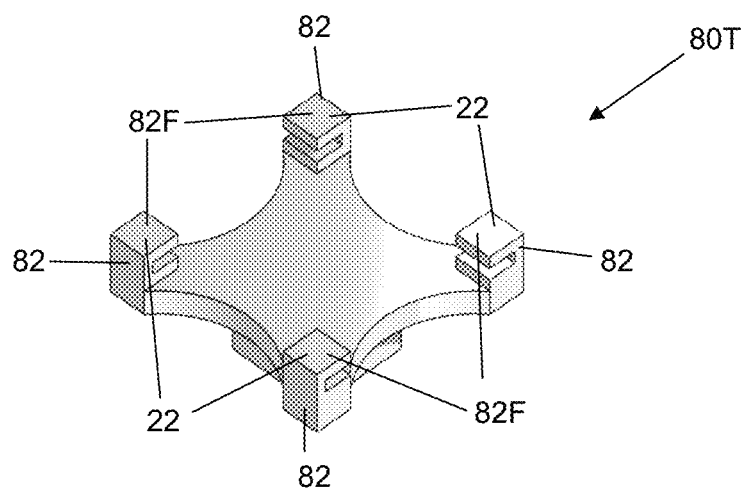
FIG. 12 is a bottom perspective view of a droplet manipulator configured to facilitate transfer of liquid droplets from one surface to another.

Other embodiments of the droplet manipulator 80 may be configured to perform liquid mixing as shown in FIG. 11, or droplet transfer as shown in FIG. 12. For example, a mixing droplet manipulator 80M as shown in FIG. 11 may comprise multiple projections 82 that have a hydrophobic surface (e.g. coated with 1% Teflon™ solution or the tip may be made of Teflon™) so that as the liquid droplet 90 is moved on another surface 102 against the downward-facing projections 82, each projection 82 passes through the droplet 90 in turn to mix the liquid in the droplet 90. For example, a transferring droplet manipulator 80T as shown in FIG. 12 may comprise multiple projections 82 that each have a flat end 82F coated with polydopamine to serve as surface energy traps 22 to remove and retain liquid droplets 22 from another surface (not shown). Although four projections 82 are shown in FIG. 12, other embodiments may have other numbers of the projections 82.

Where the droplet manipulator 80 is configured to be releasably attachable to the platform 101, releasable attachment of the droplet manipulator 80 to the platform 101 may be achieved using any appropriate means, for example, by the use of magnets provided on the droplet manipulator 80 as well as on the platform 101, or by providing the droplet manipulator 80 and platform 101 with connector elements that interlock with each other. For example, the connector elements comprise a number (at least one) of protrusions 189 provided on the platform 101 (FIG. 8a) and at least one appropriately shaped recess 89 provided at a base 80B of the droplet manipulator 80 (FIGS. 9b and 10b), wherein the protrusions 189 have a tight fit with the at least one recess 89 to allow secure attachment as well as release of the droplet manipulator 80 relative to the platform 101. In an exemplary embodiment, one recess 89 of the droplet manipulator 80 may be configured to fit therein two or four protrusions 189 on the platform 101, as may be seen in FIG. 8c. Appreciably, in other embodiments (not shown), the number of protrusions may alternatively be provided on the droplet manipulator while the at least one appropriately shaped recess may be provided on the platform.

Figure 13:
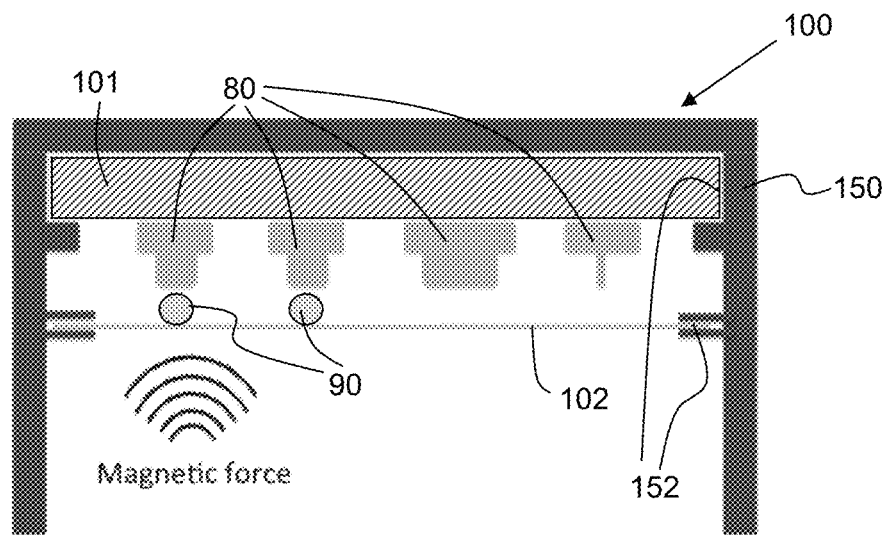
FIG. 13 is a schematic side view of the apparatus of FIG. 8a including a frame.
Figure 14:
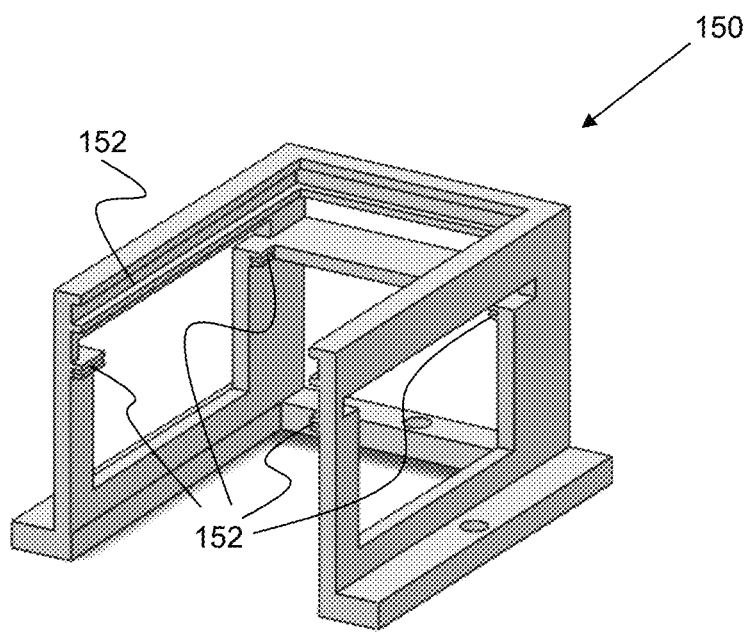
FIG. 14 is a schematic perspective view of the frame of FIG. 13.

In an exemplary embodiment of the magnetic digital microfluidic apparatus 100, multiple droplet manipulators 80 are attached to and extend downwardly from a platform 101 as shown in FIG. 13, so as to interact with liquid droplets 90 (containing magnetic particles) that are provided on a hydrophobic surface 102 and moved with a magnetic force. In an exemplary embodiment, the hydrophobic surface 102 may comprise a Goldseal® glass coverslip (48×65 mm, No. 1) dip coated in 1% Teflon™ AF solution and spin coated at 500 rpm for 40 seconds followed by baking at 120 degrees for 2 minutes and rinsing with DI water after cooling down. As shown in FIGS. 13 and 14, the apparatus 100 may further comprise a frame 150 configured to support the platform 101 on which the droplet manipulators 80 are attached as well as to support the hydrophobic surface 102 on which the droplets 90 are moved. The frame 150 may comprise appropriately configured slots 152 to allow easy placement and removal of the platform 101 with droplet manipulators 80 and the hydrophobic surface 102 from the frame 150. In an exemplary embodiment, the frame 150, platform 101 and droplet manipulators 80 may be formed by Foam2 Stereolithography (SLA) 3D printing, using a clear resin (FLGPC04) at a resolution of 500 μm.

The above described apparatus (with reference to FIGS. 8a to 14) thus provide for a pump-less leak-less and modular magnetic digital microfluidic manipulation of liquid droplets for various bioassay applications.

Whilst there has been described in the foregoing description exemplary embodiments of the present invention, it will be understood by those skilled in the technology concerned that many variations and combination in details of design, construction and/or operation may be made without departing from the present invention.

The invention claimed is:

1. A magnetic digital microfluidic apparatus for manipulating a liquid droplet containing magnetic particles using a magnetic force, the apparatus comprising:
   a hydrophobic surface on which the liquid droplet containing magnetic particles can be moved using the magnetic force;
   a droplet manipulator provided on a platform and facing the hydrophobic surface; and
   a hydrophilic surface energy trap formed on the droplet manipulator, the hydrophilic surface energy trap configured to retain at least a portion of the liquid droplet thereon when the liquid droplet moves across the hydrophobic surface to the hydrophilic surface energy trap, the hydrophilic surface energy trap comprising a layer of polydopamine.

2. The apparatus of claim 1, wherein in use, the hydrophilic surface energy trap retains all of the liquid droplet thereon while allowing the magnetic particles to be moved out of the liquid droplet by the magnetic force.

3. The apparatus of claim 1, wherein in use, the hydrophilic surface energy trap retains only a part of the liquid droplet thereon while allowing a remainder of the liquid droplet containing the magnetic particles to be moved away from the hydrophilic surface energy trap by the magnetic force.

4. The apparatus of claim 1, wherein the droplet manipulator is releasably attachable to the platform.

5. The apparatus of 1, wherein the hydrophilic surface energy trap is formed at a tip of a projection of the droplet manipulator.

6. The apparatus of claim 5, wherein the projection has a C-shaped cross-section.

7. The apparatus of claim 5, wherein a hole is provided at the tip of the projection and wherein the hydrophilic surface energy trap is formed in the hole.

8. The apparatus of claim 1, wherein the droplet manipulator comprises a mixing droplet manipulator to facilitate mixing of liquid in the liquid droplet.

9. The apparatus of claim 8, wherein the mixing droplet manipulator is releasably attachable to the platform.

10. The apparatus of claim 8, wherein the mixing droplet manipulator comprises a plurality of hydrophobic projections provided to pass through the liquid droplet.

11. The apparatus of claim 1, wherein the droplet manipulator comprises a transferring droplet manipulator to facilitate transfer of at least one liquid droplet from one hydrophobic surface to another hydrophobic surface.

12. The apparatus of claim 11, wherein the transferring droplet manipulator is releasably attachable to the platform.

13. The apparatus of claim 11, wherein the transferring droplet manipulator comprises a hydrophilic surface energy trap to remove and retain at least one liquid droplet from another surface.

14. The apparatus of claim 1, wherein the droplet manipulator is releasably attachable to the platform at any one of a plurality of selectable locations on the platform.

15. The apparatus of claim 1, wherein a shape of the portion of the liquid droplet retained by the hydrophilic surface energy trap conforms with a shape of the hydrophilic surface energy trap.

16. A method of magnetic digital microfluidic manipulation, the method comprising steps of:
  (a) applying a magnetic force to move a liquid droplet containing magnetic particles on a hydrophobic surface;
  (b) moving the liquid droplet using the magnetic force across the hydrophobic surface to a polydopamine surface energy trap formed on a droplet manipulator facing the hydrophobic surface;
  (c) contacting the liquid droplet on the hydrophobic surface with the polydopamine surface energy trap; and
  (d) retaining at least a portion of the liquid droplet on the polydopamine surface energy trap.

17. The method of claim 16, wherein step (d) comprises retaining all of the liquid droplet on the polydopamine surface energy trap, and the method further comprises a step (e) of moving the magnetic particles out of the liquid droplet retained on the polydopamine surface energy trap.

18. The method of claim 16, wherein step (d) comprises retaining only a part of the liquid droplet on the polydopamine surface energy trap, and the method further comprises a step (e) of moving a remainder of the liquid droplet and the magnetic particles away from the part of the liquid droplet retained on the polydopamine surface energy trap.

* * * * *